(12) United States Patent
Deckman et al.

(10) Patent No.: US 11,259,825 B2
(45) Date of Patent: Mar. 1, 2022

(54) DEVICES AND METHODS FOR TREATMENT OF TISSUE

(71) Applicant: Gynesonics, Inc., Redwood City, CA (US)

(72) Inventors: Robert K. Deckman, San Bruno, CA (US); Craig Gerbi, Mountain View, CA (US); Michael Munrow, Belmont, CA (US); Jessica Grossman, Covington, KY (US)

(73) Assignee: Gynesonics, Inc., Redwood City, CA (US)

( * ) Notice: Subject to any disclaimer, the term of this patent is extended or adjusted under 35 U.S.C. 154(b) by 991 days.

(21) Appl. No.: 15/628,166

(22) Filed: Jun. 20, 2017

(65) Prior Publication Data
US 2017/0290626 A1 Oct. 12, 2017

Related U.S. Application Data

(63) Continuation of application No. 13/667,891, filed on Nov. 2, 2012, now Pat. No. 10,058,342, which is a
(Continued)

(51) Int. Cl.
*A61B 8/00* (2006.01)
*A61B 17/225* (2006.01)
(Continued)

(52) U.S. Cl.
CPC .......... *A61B 17/2256* (2013.01); *A61B 8/085* (2013.01); *A61B 8/0833* (2013.01);
(Continued)

(58) Field of Classification Search
None
See application file for complete search history.

(56) References Cited

U.S. PATENT DOCUMENTS

| 4,289,132 A | 9/1981 | Rieman |
| 4,802,487 A | 2/1989 | Martin et al. |

(Continued)

FOREIGN PATENT DOCUMENTS

| WO | WO-9528129 A1 | 10/1995 |
| WO | WO-9717105 A1 | 5/1997 |

(Continued)

OTHER PUBLICATIONS

Alterovitz, et al. Simulating Needle Insertion and Radioactive Seed Implantation for Prostate Brachytherapy. Medicine Meets Virtual Reality 11, Westwood et al. (Eds.), IOS Press, Jan. 2003, pp. 19-25.
(Continued)

*Primary Examiner* — Joel F Brutus
(74) *Attorney, Agent, or Firm* — Wilson Sonsini Goodrich & Rosati

(57) ABSTRACT

Delivery systems, and methods using the same, having an ultrasound viewing window for improved imaging and a needle for ablation treatment of target tissues. In an embodiment, the target tissue is a fibroid within a female's uterus. In an embodiment, the delivery system includes a rigid shaft having a proximal end, a distal end, and an axial passage extending through the rigid shaft. In an embodiment, the axial passage is configured for removably receiving the ultrasound imaging insert having an ultrasound array disposed a distal portion.

20 Claims, 23 Drawing Sheets

Related U.S. Application Data continuation-in-part of application No. 12/973,587, filed on Dec. 20, 2010, now Pat. No. 8,506,485, which is a continuation of application No. 11/564,164, filed on Nov. 28, 2006, now Pat. No. 7,874,986, which is a continuation-in-part of application No. 11/409,496, filed on Apr. 20, 2006, now Pat. No. 7,815,571, said application No. 13/667,891 is a continuation-in-part of application No. 11/620,591, filed on Jan. 5, 2007, now Pat. No. 9,357,977.

(60) Provisional application No. 60/758,881, filed on Jan. 12, 2006.

(51) Int. Cl.
*A61B 8/08* (2006.01)
*A61B 8/12* (2006.01)
*A61B 18/14* (2006.01)
*A61B 90/00* (2016.01)
*A61B 17/42* (2006.01)
*A61B 18/00* (2006.01)
*A61B 18/18* (2006.01)
*A61B 17/00* (2006.01)

(52) U.S. Cl.
CPC .............. *A61B 8/0841* (2013.01); *A61B 8/12* (2013.01); *A61B 8/44* (2013.01); *A61B 8/445* (2013.01); *A61B 8/4411* (2013.01); *A61B 18/1477* (2013.01); *A61B 18/18* (2013.01); *A61B 2017/00106* (2013.01); *A61B 2017/4216* (2013.01); *A61B 2018/00559* (2013.01); *A61B 2018/00577* (2013.01); *A61B 2090/3784* (2016.02)

(56) References Cited

U.S. PATENT DOCUMENTS

| | | | |
|---|---|---|---|
| 4,869,258 A | 9/1989 | Hetz | |
| 4,936,281 A | 6/1990 | Stasz | |
| 5,000,185 A | 3/1991 | Yock | |
| 5,090,414 A | 2/1992 | Takano | |
| 5,190,050 A | 3/1993 | Nitzsche | |
| 5,315,741 A | 5/1994 | Dubberke | |
| 5,335,663 A | 8/1994 | Oakley et al. | |
| 5,372,138 A | 12/1994 | Crowley et al. | |
| 5,372,587 A | 12/1994 | Hammerslag et al. | |
| 5,456,689 A | 10/1995 | Kresch et al. | |
| 5,469,853 A | 11/1995 | Law et al. | |
| 5,471,988 A | 12/1995 | Fujio et al. | |
| 5,474,075 A | 12/1995 | Goldberg et al. | |
| 5,492,126 A | 2/1996 | Hennige et al. | |
| 5,527,331 A | 6/1996 | Kresch et al. | |
| 5,531,676 A | 7/1996 | Edwards et al. | |
| 5,649,911 A | 7/1997 | Trerotola | |
| 5,662,664 A | 9/1997 | Gordon et al. | |
| 5,666,954 A | 9/1997 | Chapelon et al. | |
| 5,697,897 A | 12/1997 | Buchholtz et al. | |
| 5,730,752 A | 3/1998 | Alden et al. | |
| 5,741,287 A | 4/1998 | Alden et al. | |
| 5,752,518 A | 5/1998 | McGee et al. | |
| 5,769,880 A | 6/1998 | Truckai et al. | |
| 5,800,378 A | 9/1998 | Edwards et al. | |
| 5,842,994 A | 12/1998 | Tenhoff et al. | |
| 5,853,368 A | 12/1998 | Solomon et al. | |
| 5,860,974 A | 1/1999 | Abele | |
| 5,863,294 A | 1/1999 | Alden | |
| 5,873,828 A | 2/1999 | Fujio et al. | |
| 5,876,340 A | 3/1999 | Tu et al. | |
| 5,876,399 A | 3/1999 | Chia et al. | |
| 5,891,137 A | 4/1999 | Chia et al. | |
| 5,906,615 A | 5/1999 | Thompson | |
| 5,916,198 A | 6/1999 | Dillow | |
| 5,957,941 A | 9/1999 | Ream | |
| 5,964,740 A | 10/1999 | Ouchi | |
| 5,979,452 A | 11/1999 | Fogarty et al. | |
| 5,979,453 A * | 11/1999 | Savage | A61B 18/1477 128/898 |
| 5,984,942 A | 11/1999 | Alden et al. | |
| 6,002,968 A | 12/1999 | Edwards | |
| 6,007,499 A | 12/1999 | Martin et al. | |
| 6,032,673 A | 3/2000 | Savage et al. | |
| 6,039,748 A | 3/2000 | Savage et al. | |
| 6,059,766 A | 5/2000 | Greff | |
| 6,077,257 A | 6/2000 | Edwards et al. | |
| 6,141,577 A | 10/2000 | Rolland et al. | |
| 6,146,378 A | 11/2000 | Mikus et al. | |
| 6,146,380 A | 11/2000 | Racz et al. | |
| 6,158,250 A | 12/2000 | Tibbals, Jr. et al. | |
| 6,171,249 B1 | 1/2001 | Chin et al. | |
| 6,190,383 B1 | 2/2001 | Schmaltz et al. | |
| 6,193,714 B1 | 2/2001 | McGaffigan et al. | |
| 6,211,153 B1 | 4/2001 | Garnick et al. | |
| 6,238,336 B1 | 5/2001 | Ouchi | |
| 6,254,601 B1 | 7/2001 | Burbank et al. | |
| 6,280,441 B1 | 8/2001 | Ryan | |
| 6,296,639 B1 | 10/2001 | Truckai et al. | |
| 6,306,097 B1 | 10/2001 | Park et al. | |
| 6,306,129 B1 | 10/2001 | Little et al. | |
| 6,315,741 B1 | 11/2001 | Martin et al. | |
| 6,379,348 B1 | 4/2002 | Onik | |
| 6,405,732 B1 | 6/2002 | Edwards et al. | |
| 6,419,048 B1 | 7/2002 | Robinson et al. | |
| 6,419,648 B1 | 7/2002 | Vitek et al. | |
| 6,419,653 B2 | 7/2002 | Edwards et al. | |
| 6,419,673 B1 | 7/2002 | Edwards et al. | |
| 6,425,867 B1 | 7/2002 | Vaezy et al. | |
| 6,432,067 B1 | 8/2002 | Martin et al. | |
| 6,447,477 B2 | 9/2002 | Burney et al. | |
| 6,461,296 B1 | 10/2002 | Desai | |
| 6,463,331 B1 | 10/2002 | Edwards | |
| 6,468,228 B1 | 10/2002 | Topel et al. | |
| 6,475,152 B1 | 11/2002 | Kelly, Jr. et al. | |
| 6,482,203 B2 | 11/2002 | Paddock et al. | |
| 6,485,413 B1 | 11/2002 | Boppart et al. | |
| 6,506,154 B1 | 1/2003 | Ezion et al. | |
| 6,506,156 B1 | 1/2003 | Jones et al. | |
| 6,506,171 B1 | 1/2003 | Vitek et al. | |
| 6,507,747 B1 | 1/2003 | Gowda et al. | |
| 6,508,815 B1 | 1/2003 | Strul et al. | |
| 6,522,142 B1 | 2/2003 | Freundlich | |
| 6,526,320 B2 | 2/2003 | Mitchell | |
| 6,540,677 B1 | 4/2003 | Angelsen et al. | |
| 6,543,272 B1 | 4/2003 | Vitek | |
| 6,550,482 B1 | 4/2003 | Burbank et al. | |
| 6,554,780 B1 | 4/2003 | Sampson et al. | |
| 6,554,801 B1 | 4/2003 | Steward et al. | |
| 6,559,644 B2 | 5/2003 | Froundlich et al. | |
| 6,569,159 B1 | 5/2003 | Edwards et al. | |
| 6,572,613 B1 | 6/2003 | Ellman et al. | |
| 6,589,237 B2 | 7/2003 | Woloszko et al. | |
| 6,592,559 B1 | 7/2003 | Pakter et al. | |
| 6,602,251 B2 | 8/2003 | Burbank et al. | |
| 6,610,054 B1 | 8/2003 | Edwards et al. | |
| 6,612,988 B2 | 9/2003 | Maor et al. | |
| 6,613,004 B1 | 9/2003 | Vitek et al. | |
| 6,613,005 B1 | 9/2003 | Friedman et al. | |
| 6,623,481 B1 | 9/2003 | Garbagnati et al. | |
| 6,626,854 B2 | 9/2003 | Friedman et al. | |
| 6,626,855 B1 | 9/2003 | Weng et al. | |
| 6,632,193 B1 | 10/2003 | Davison et al. | |
| 6,635,055 B1 | 10/2003 | Cronin | |
| 6,635,065 B2 | 10/2003 | Burbank et al. | |
| 6,638,275 B1 | 10/2003 | McGaffigan et al. | |
| 6,638,286 B1 | 10/2003 | Burbank et al. | |
| 6,645,162 B2 | 11/2003 | Friedman et al. | |
| 6,652,516 B1 | 11/2003 | Gough | |
| 6,654,202 B2 | 11/2003 | Rea et al. | |
| 6,660,002 B1 | 12/2003 | Edwards et al. | |
| 6,660,024 B1 | 12/2003 | Flaherty et al. | |
| 6,662,680 B2 * | 12/2003 | Rocket | B62K 21/125 74/551.1 |

(56) References Cited

U.S. PATENT DOCUMENTS

| | | |
|---|---|---|
| 6,663,624 B2 | 12/2003 | Edwards et al. |
| 6,663,626 B2 | 12/2003 | Truckai et al. |
| 6,666,833 B1 | 12/2003 | Friedman et al. |
| 6,669,643 B1 | 12/2003 | Dubinsky |
| 6,679,855 B2 | 1/2004 | Horn et al. |
| 6,685,639 B1 | 2/2004 | Wang et al. |
| 6,689,128 B2 | 2/2004 | Sliwa et al. |
| 6,692,490 B1 | 2/2004 | Edwards |
| 6,701,931 B2 | 3/2004 | Sliwa et al. |
| 6,705,994 B2 | 3/2004 | Vortman et al. |
| 6,712,815 B2 | 3/2004 | Sampson et al. |
| 6,716,184 B2 | 4/2004 | Vaezy et al. |
| 6,719,755 B2 | 4/2004 | Sliwa et al. |
| 6,728,571 B1 | 4/2004 | Barbato |
| 6,730,081 B1 | 5/2004 | Desai |
| 6,735,461 B2 | 5/2004 | Vitek et al. |
| 6,743,184 B2 | 6/2004 | Sampson et al. |
| 6,746,447 B2 | 6/2004 | Davison et al. |
| 6,764,488 B1 | 7/2004 | Burbank et al. |
| 6,773,431 B2 | 8/2004 | Eggers et al. |
| 6,790,180 B2 | 9/2004 | Vitek |
| 6,805,128 B1 | 10/2004 | Pless et al. |
| 6,805,129 B1 | 10/2004 | Pless et al. |
| 6,813,520 B2 | 11/2004 | Truckai et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,840,935 B2 | 1/2005 | Lee |
| 6,936,048 B2 | 8/2005 | Hurst |
| 6,938,048 B1 | 8/2005 | Jilk et al. |
| 6,944,490 B1 | 9/2005 | Chow |
| 6,969,354 B1 | 11/2005 | Marian |
| 6,994,706 B2 | 2/2006 | Chornenky et al. |
| 7,160,296 B2 | 1/2007 | Pearson et al. |
| 7,229,401 B2 | 6/2007 | Kindlein |
| 7,247,141 B2 | 7/2007 | Makin et al. |
| 7,331,957 B2 | 2/2008 | Woloszko et al. |
| 7,387,628 B1 | 6/2008 | Behl et al. |
| 7,517,346 B2 | 4/2009 | Sloan et al. |
| 7,549,424 B2 | 6/2009 | Desai |
| 7,771,357 B2 | 8/2010 | Burbank et al. |
| 7,815,571 B2 | 10/2010 | Gerbi et al. |
| 7,874,986 B2 | 1/2011 | Deckman et al. |
| 7,918,795 B2 | 4/2011 | Grossman |
| 7,963,941 B2 | 6/2011 | Wilk |
| 8,080,009 B2 | 12/2011 | Lee et al. |
| 8,088,072 B2 | 1/2012 | Munrow et al. |
| 8,157,741 B2 | 4/2012 | Hirota |
| 8,157,745 B2 | 4/2012 | Schoot |
| 8,216,231 B2 | 7/2012 | Behl et al. |
| 8,221,321 B2 | 7/2012 | McMorrow et al. |
| 8,287,485 B2 | 10/2012 | Kimura et al. |
| 8,377,041 B2 | 2/2013 | Frassica et al. |
| 8,469,893 B2 | 6/2013 | Chiang et al. |
| 8,506,485 B2 | 8/2013 | Deckman et al. |
| 8,512,330 B2 | 8/2013 | Epstein et al. |
| 8,512,333 B2 | 8/2013 | Epstein et al. |
| 8,540,634 B2 | 9/2013 | Bruce et al. |
| 8,585,598 B2 | 11/2013 | Razzaque et al. |
| 8,622,911 B2 | 1/2014 | Hossack et al. |
| 8,663,130 B2 | 3/2014 | Neubach et al. |
| 8,718,339 B2 | 5/2014 | Tonomura et al. |
| 8,814,796 B2 | 8/2014 | Martin et al. |
| 8,992,427 B2 | 3/2015 | Munrow et al. |
| 9,089,287 B2 | 7/2015 | Sliwa et al. |
| 9,198,707 B2 | 12/2015 | McKay et al. |
| 9,198,719 B2 | 12/2015 | Murdeshwar et al. |
| 9,247,925 B2 | 2/2016 | Havel et al. |
| 9,357,977 B2 | 6/2016 | Grossman |
| 9,439,627 B2 | 9/2016 | Case et al. |
| 9,510,898 B2 | 12/2016 | Epstein et al. |
| 9,516,996 B2 | 12/2016 | Diolaiti et al. |
| 9,517,047 B2 | 12/2016 | Grossman |
| 9,987,080 B2 | 6/2018 | Grossman |
| 10,182,862 B2 | 1/2019 | Grossman |
| 2001/0014805 A1* | 8/2001 | Burbank .............. A61B 8/0833 606/45 |
| 2001/0051802 A1 | 12/2001 | Woloszko et al. |
| 2002/0002393 A1 | 1/2002 | Mitchell |
| 2002/0022835 A1 | 2/2002 | Lee |
| 2002/0052600 A1 | 5/2002 | Davison et al. |
| 2002/0068871 A1 | 6/2002 | Mendlein et al. |
| 2002/0077550 A1 | 6/2002 | Rabiner et al. |
| 2002/0156373 A1 | 10/2002 | Wakabayashi et al. |
| 2002/0183735 A1 | 12/2002 | Edwards et al. |
| 2003/0009164 A1 | 1/2003 | Woloszko et al. |
| 2003/0014046 A1 | 1/2003 | Edwards et al. |
| 2003/0028111 A1 | 2/2003 | Vaezy et al. |
| 2003/0032896 A1 | 2/2003 | Bosley et al. |
| 2003/0045768 A1* | 3/2003 | Hirooka .............. A61B 8/0816 600/2 |
| 2003/0114732 A1 | 6/2003 | Webler et al. |
| 2003/0130575 A1 | 7/2003 | Desai |
| 2003/0130655 A1 | 7/2003 | Woloszko et al. |
| 2003/0130665 A1 | 7/2003 | Pinczewski et al. |
| 2003/0195420 A1 | 10/2003 | Mendlein et al. |
| 2003/0195496 A1 | 10/2003 | Maguire et al. |
| 2003/0199472 A1 | 10/2003 | Al-Hendy et al. |
| 2003/0216725 A1 | 11/2003 | Woloszko et al. |
| 2003/0216759 A1 | 11/2003 | Burbank et al. |
| 2004/0002699 A1 | 1/2004 | Ryan et al. |
| 2004/0006336 A1 | 1/2004 | Swanson |
| 2004/0030268 A1 | 2/2004 | Weng et al. |
| 2004/0054366 A1 | 3/2004 | Davison et al. |
| 2004/0082883 A1 | 4/2004 | Kohno |
| 2004/0120668 A1 | 6/2004 | Loeb |
| 2004/0143252 A1 | 7/2004 | Hurst |
| 2004/0153057 A1 | 8/2004 | Davison |
| 2004/0175399 A1 | 9/2004 | Schiffman |
| 2004/0176402 A1 | 9/2004 | Qiu |
| 2004/0193028 A1 | 9/2004 | Jones et al. |
| 2004/0193238 A1* | 9/2004 | Mosher .............. A61B 17/0625 607/99 |
| 2004/0199179 A1 | 10/2004 | Elliott |
| 2004/0215182 A1 | 10/2004 | Lee |
| 2004/0230190 A1 | 11/2004 | Dahla et al. |
| 2004/0254572 A1 | 12/2004 | McIntyre et al. |
| 2005/0038340 A1 | 2/2005 | Vaezy et al. |
| 2005/0085730 A1 | 4/2005 | Flesch et al. |
| 2005/0096647 A1 | 5/2005 | Steinke et al. |
| 2005/0107781 A1 | 5/2005 | Ostrovsky et al. |
| 2005/0124882 A1 | 6/2005 | Ladabaum et al. |
| 2005/0149013 A1 | 7/2005 | Lee |
| 2005/0177209 A1 | 8/2005 | Leung et al. |
| 2005/0197577 A1 | 9/2005 | Makin et al. |
| 2005/0203410 A1* | 9/2005 | Jenkins ................ A61B 8/0883 600/459 |
| 2005/0215990 A1 | 9/2005 | Govari |
| 2005/0216039 A1 | 9/2005 | Lederman |
| 2005/0228288 A1 | 10/2005 | Hurst |
| 2005/0255039 A1 | 11/2005 | Desai |
| 2005/0256405 A1 | 11/2005 | Makin et al. |
| 2006/0010207 A1 | 1/2006 | Akerman et al. |
| 2006/0018665 A1 | 1/2006 | Shibata et al. |
| 2006/0058680 A1 | 3/2006 | Solomon |
| 2006/0178665 A1 | 8/2006 | Sloan et al. |
| 2006/0184049 A1 | 8/2006 | Tsujita |
| 2006/0189972 A1 | 8/2006 | Grossman |
| 2006/0241368 A1 | 10/2006 | Fichtinger et al. |
| 2007/0006215 A1 | 1/2007 | Epstein et al. |
| 2007/0161905 A1 | 7/2007 | Munrow |
| 2007/0249936 A1 | 10/2007 | Deckman et al. |
| 2007/0249939 A1 | 10/2007 | Gerbi et al. |
| 2008/0033493 A1 | 2/2008 | Deckman et al. |
| 2008/0228081 A1 | 9/2008 | Becker et al. |
| 2009/0043295 A1 | 2/2009 | Arnal et al. |
| 2009/0131790 A1 | 5/2009 | Munrow et al. |
| 2009/0287081 A1 | 11/2009 | Grossman et al. |
| 2010/0056926 A1 | 3/2010 | Deckman et al. |
| 2010/0262133 A1 | 10/2010 | Hoey et al. |
| 2011/0087100 A1 | 4/2011 | Grossman |
| 2011/0288412 A1 | 11/2011 | Deckman et al. |
| 2012/0035474 A1 | 2/2012 | Deckman et al. |
| 2012/0071794 A1 | 3/2012 | Karni |

(56) References Cited

U.S. PATENT DOCUMENTS

| | | |
|---|---|---|
| 2012/0078134 A1 | 3/2012 | Munrow et al. |
| 2012/0165813 A1 | 6/2012 | Lee et al. |
| 2012/0209115 A1 | 8/2012 | Tonomura |
| 2012/0277737 A1 | 11/2012 | Curley |
| 2012/0316440 A1 | 12/2012 | Munrow et al. |
| 2013/0281863 A1 | 10/2013 | Chiang et al. |
| 2013/0296699 A1 | 11/2013 | Deckman et al. |
| 2013/0317366 A1 | 11/2013 | Hirayama et al. |
| 2014/0180273 A1 | 6/2014 | Nair |
| 2014/0276081 A1 | 9/2014 | Tegels |
| 2015/0150497 A1 | 6/2015 | Goldchmit |
| 2015/0173592 A1 | 6/2015 | Leeflang et al. |
| 2015/0257779 A1 | 9/2015 | Sinelnikov et al. |
| 2016/0151041 A1 | 6/2016 | Lee et al. |
| 2016/0278740 A1 | 9/2016 | Negrila et al. |
| 2016/0310042 A1 | 10/2016 | Kesten et al. |
| 2018/0078303 A1 | 3/2018 | Grossman |
| 2019/0192217 A1 | 6/2019 | Grossman |

FOREIGN PATENT DOCUMENTS

| | | |
|---|---|---|
| WO | WO-9811834 A1 | 3/1998 |
| WO | WO-9814169 A1 | 4/1998 |
| WO | WO-9943366 A1 | 9/1999 |
| WO | WO-0000098 A1 | 1/2000 |
| WO | WO-0180723 A2 | 11/2001 |
| WO | WO-0195819 A1 | 12/2001 |
| WO | WO-0211639 A1 | 2/2002 |
| WO | WO-0180723 A3 | 4/2002 |
| WO | WO-03005882 A2 | 1/2003 |
| WO | WO-03065908 A1 | 8/2003 |
| WO | WO-03088833 A1 | 10/2003 |
| WO | WO-03005882 A3 | 11/2003 |
| WO | WO-2004002293 A2 | 1/2004 |
| WO | WO-2004002550 A2 | 1/2004 |
| WO | WO-2004020011 A1 | 3/2004 |
| WO | WO-2004035110 A2 | 4/2004 |
| WO | WO-2004035110 A3 | 6/2004 |
| WO | WO-2004058328 A2 | 7/2004 |
| WO | WO-2004064658 A1 | 8/2004 |
| WO | WO-2004002550 A3 | 10/2004 |
| WO | WO-2004058328 A3 | 10/2004 |
| WO | WO-2004002293 A3 | 7/2005 |
| WO | WO-2007124265 A2 | 11/2007 |
| WO | WO-2007149595 A2 | 12/2007 |
| WO | WO-2014039795 A1 | 3/2014 |

OTHER PUBLICATIONS

Bergamini, et al. Laparoscopic Radiofrequency Thermal Ablation: A New Approach to Symptomatic Uterine Myomas. Am. J. Obstetrics and Gynecology (2005) 192: 768-73.

CNN.com Health Women. Experimental technique uses lasers to shrink uterine fibroids. Nov. 28, 2000.

Co-pending U.S. Appl. No. 15/634,368, filed Jun. 27, 2017.

European Office Action dated Apr. 21, 2016 for EP07760319.9.

Extended European search report and search opinion dated Nov. 23, 2010 for EP 07760319.9.

Hindley, et al. MRI guidance of focused ultrasound therapy of uterine fibroids: Early results. American Journal of Roentgenology, 2004, 183(6): 1173-1719.

International search report and written opinion dated Nov. 13, 2007 for PCT/US2007/066235.

Kanaoka, et al. Microwave endometrial ablation at a frequency of 2.45 Ghz. A pilot study. J Reprod Med. Jun. 2001; 46(60): 559-63.

Law, et al. Magnetic resonance-guided percutaneous laser ablation of uterine fibroids. J Magn Reson Imaging. Oct. 2000; 12(4):565-70.

Liu, et al. Catheter-Based Intraluminal Sonography. J. Ultrasound Med., 2004, 23:145-160.

Mogami, et al. Usefulness of MR-guided percutaneous cryotherapy. Med. Imaging Technol. 2004, 22(3): 131-6. (English abstract).

MSNBC Online Articles, About US: Articles; "Intrauerine Fibroids Can Now Be Treated Nonsurgically" http://www.fibroids.com/news-blog/2004/08/intrauterine-fibroids-can-now-be-treated-nonsurgically/ Aug. 23, 2004.

Notice of allowance dated May 8, 2013 for U.S. Appl. No. 12/973,587.

Notice of allowance dated Jul. 22, 2010 for U.S. Appl. No. 11/409,496.

Notice of allowance dated Sep. 16, 2010 for U.S. Appl. No. 11/564,164.

Office action dated Jan. 7, 2009 for U.S. Appl. No. 11/564,164.

Office action dated Feb. 26, 2013 for U.S. Appl. No. 12/973,587.

Office action dated Mar. 3, 2010 for U.S. Appl. No. 11/564,164.

Office action dated Jun. 13, 2012 for U.S. Appl. No. 12/973,587.

Office action dated Jun. 18, 2015 for U.S. Appl. No. 13/667,891.

Office action dated Jul. 19, 2010 for U.S. Appl. No. 11/564,164.

Office action dated Jul. 22, 2009 for U.S. Appl. No. 11/409,496.

Office action dated Sep. 23, 2009 for U.S. Appl. No. 11/564,164.

Office action dated Sep. 24, 2012 for U.S. Appl. No. 12/973,587.

Office action dated Nov. 3, 2014 for U.S. Appl. No. 13/667,891.

Office action dated Dec. 23, 2009 for U.S. Appl. No. 11/409,496.

Office action dated Dec. 24, 2008 for U.S. Appl. No. 11/409,496.

Okamura, et al. Force Modeling for Needle Insertion into Soft Tissue. IEEE Transactions on Biomedical Engineering, Oct. 2001, 10 (51): 1707-1716.

RSNA 2000 Explore News Release. Lasers Liquefy Uterine Fibroid Tumors. 11:30 a.m. CST, Monday, Nov. 27, 2000.

Senoh, et al. Saline Infusion Contrast Intrauterine Sonographic Assessment of the Endometrium with High-Frequency, Real-Time Miniature Transducer Normal Menstrual Cycle: a Preliminary Report. Human Reproduction, 14 (10): 2600-2603, 1999.

Vascular and Interventional Radiology, SRSC; Nonsurgical Treatment of Uterine Fibroids. Available at http://www.drfibroid.com/treatment.htm. Accessed Apr. 11, 2011.

WebSand, Inc., New treatment options for fibroid tumors, Copyright 2002 by WebSand, Inc.

International Search Report and Written Opinion dated Jan. 17, 2018 for International PCT Patent Application No. PCT/US2017/061366.

International search report and written opinion dated Mar. 3, 2008 for PCT/US2007/060306.

Notice of allowance dated Feb. 25, 2016 for U.S. Appl. No. 11/620,594.

Notice of Allowance dated Mar. 13, 2018 for U.S. Appl. No. 15/720,199.

Notice of Allowance dated Jul. 19, 2017 for U.S. Appl. No. 12/973,642.

Notice of Allowance dated Aug. 10, 2017 for U.S. Appl. No. 12/973,642.

Notice of Allowance dated Sep. 21, 2016 for U.S. Appl. No. 15/150,813.

Notice of allowance dated Oct. 5, 2010 for U.S. Appl. No. 11/347,018.

Notice of Allowance dated Oct. 21, 2016 for U.S. Appl. No. 15/150,813.

Office action dated Jan. 21, 2015 for U.S. Appl. No. 12/973,642.

Office action dated Jan. 23, 2009 for U.S. Appl. No. 11/347,018.

Office action dated Feb. 25, 2013 for U.S. Appl. No. 12/973,642.

Office action dated Mar. 20, 2014 for U.S. Appl. No. 12/973,642.

Office action dated Apr. 2, 2010 for U.S. Appl. No. 11/620,594.

Office action dated Apr. 6, 2016 for U.S. Appl. No. 12/973,642.

Office action dated May 25, 2012 for U.S. Appl. No. 12/973,642.

Office action dated Jun. 18, 2012 for U.S. Appl. No. 11/620,594.

Office action dated Aug. 28, 2012 for U.S. Appl. No. 11/620,594.

Office action dated Sep. 17, 2009 for U.S. Appl. No. 11/347,018.

Office Action dated Oct. 21, 2016 for U.S. Appl. No. 12/973,642.

Office action dated Oct. 22, 2015 for U.S. Appl. No. 12/973,642.

Office action dated Nov. 3, 2010 for U.S. Appl. No. 11/620,594.

Office action dated Nov. 6, 2013 for U.S. Appl. No. 12/973,642.

Office Action dated Nov. 17, 2017 for U.S. Appl. No. 15/720,199.

Office action dated Dec. 22, 2009 for U.S. Appl. No. 11/347,018.

Supplementary European search report and search opinion dated Oct. 29, 2009 for EP 07797073.9.

U.S. Appl. No. 13/667,891 Notice of Allowance dated Mar. 1, 2018.

Office action dated Jun. 2, 2020 for U.S. Appl. No. 15/634,368.

(56) References Cited

OTHER PUBLICATIONS

Office action dated Jul. 27, 2020 for U.S. Appl. No. 15/824,511.

* cited by examiner

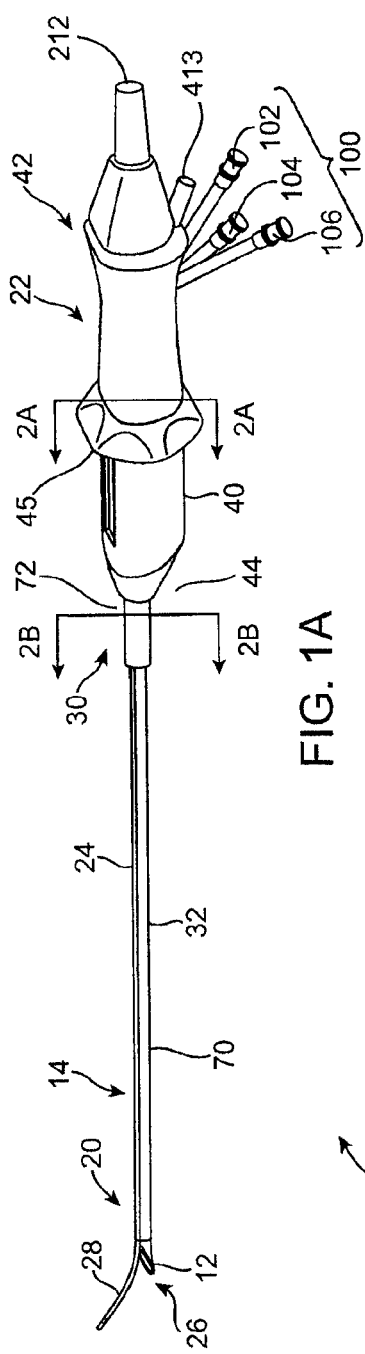
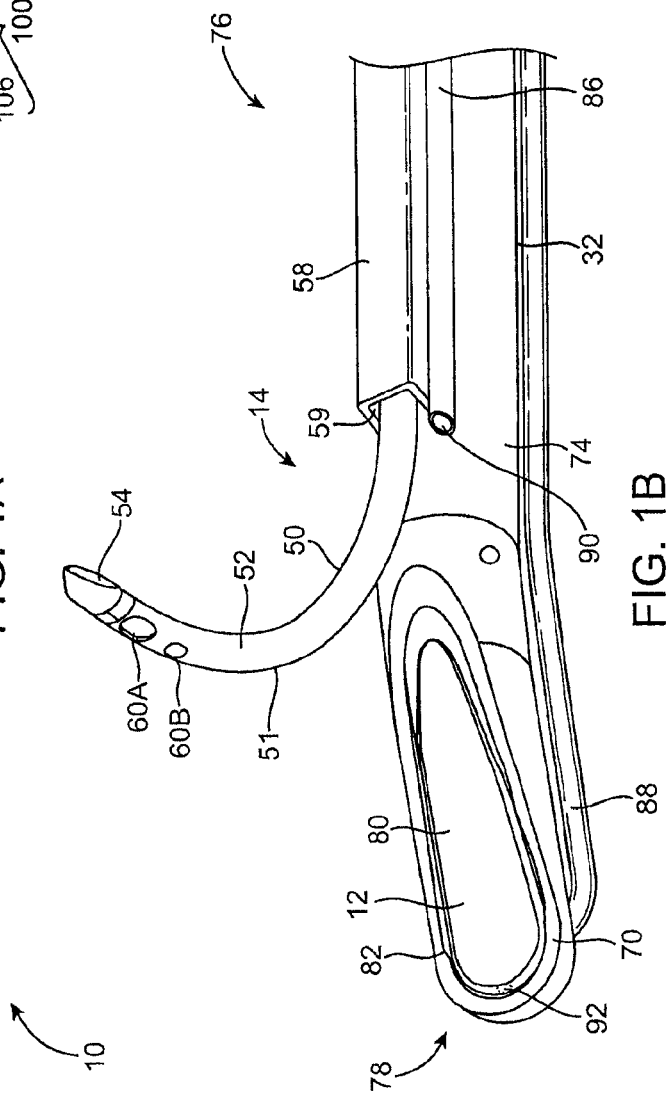
FIG. 1A
FIG. 1B

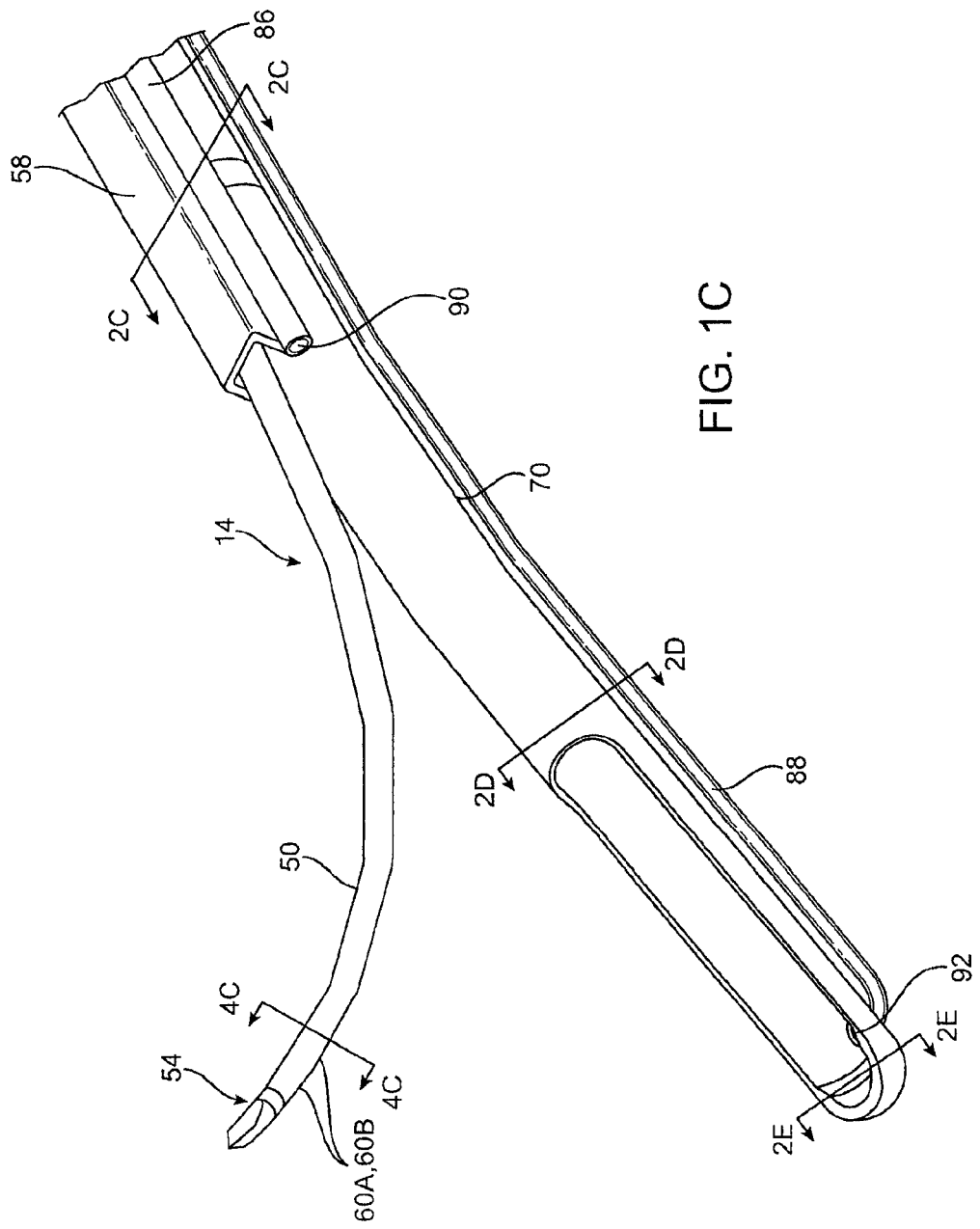

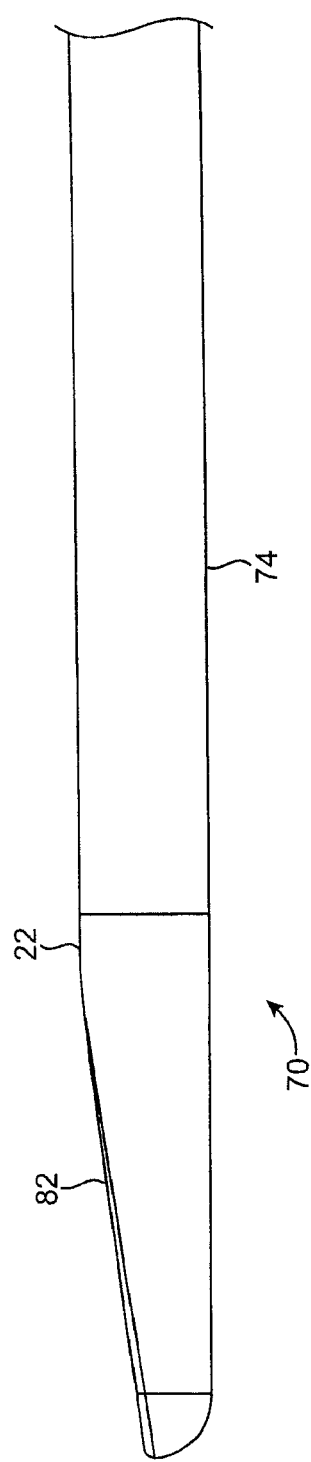
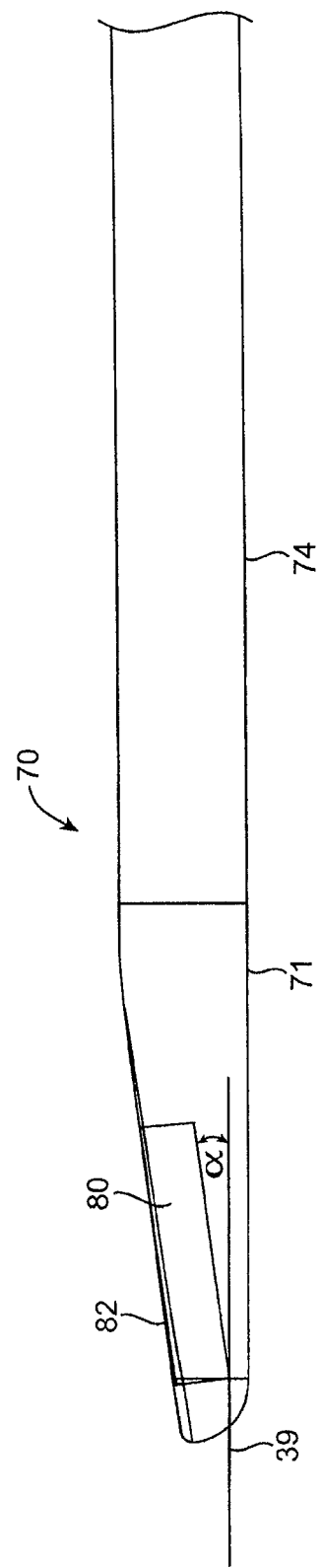

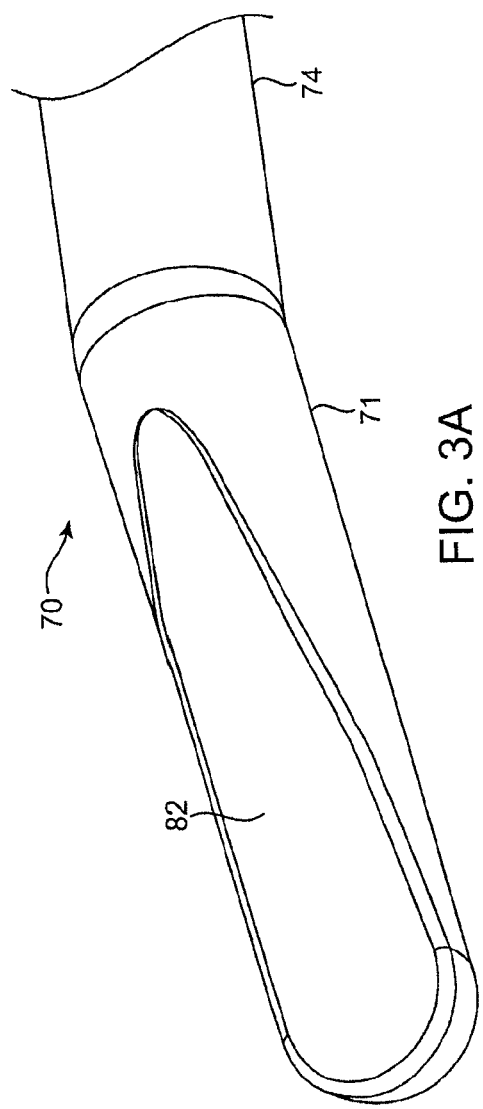
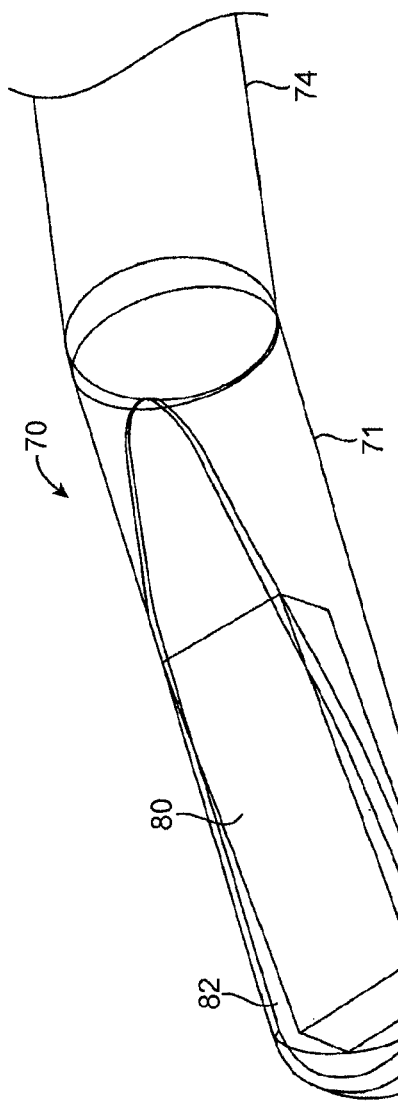
FIG. 3A
FIG. 3B

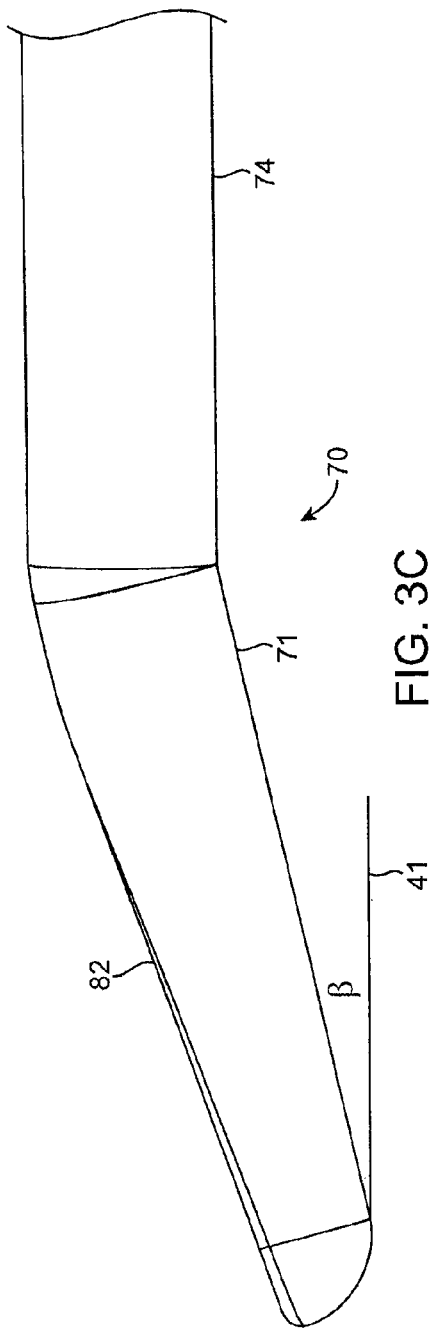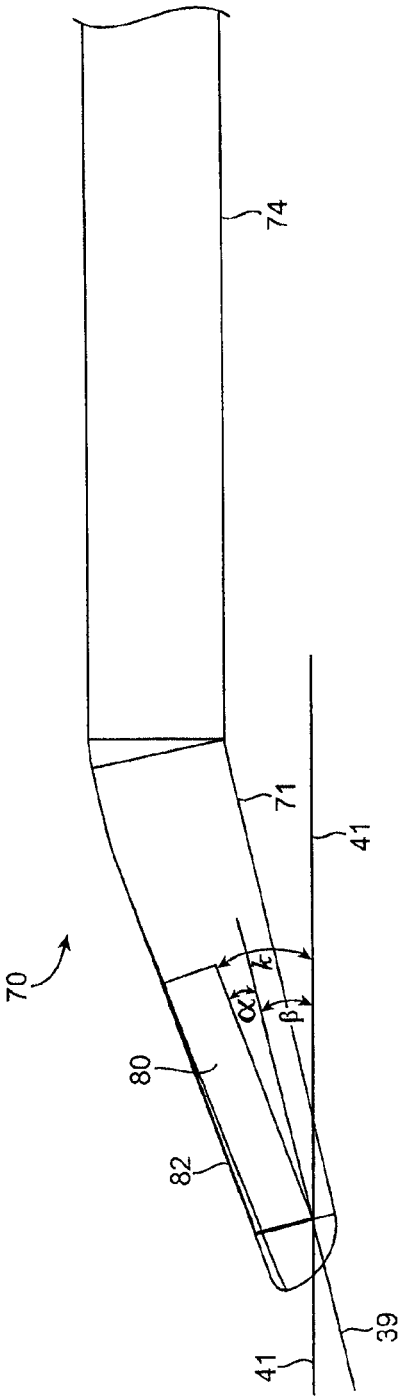

DEVICES AND METHODS FOR TREATMENT OF TISSUE

CROSS-REFERENCE TO RELATED APPLICATION

This application is a continuation of U.S. application Ser. No. 13/667,891, filed Nov. 2, 2012, now U.S. Pat. No. 10,058,342; which is a continuation-in-part of U.S. application Ser. No. 12/973,587, filed Dec. 20, 2010, now U.S. Pat. No. 8,506,485; which is a continuation of U.S. application Ser. No. 11/564,164, filed Nov. 28, 2006, now U.S. Pat. No. 7,874,986; which is a continuation-in-part of U.S. application Ser. No. 11/409,496, filed Apr. 20, 2006, now U.S. Pat. No. 7,815,571; the full disclosures of which are incorporated herein by reference; U.S. application Ser. No. 13/667,891 is also a continuation-in-part of U.S. application Ser. No. 11/620,594, filed Jan. 5, 2007, now U.S. Pat. No. 9,357,977; which claims the benefit of Provisional Application 60/758,881, filed Jan. 12, 2006, the full disclosures of which are incorporated herein by reference.

BACKGROUND OF THE INVENTION

1. Field of the Invention. The present invention relates generally to medical systems and methods. More particularly, the invention relates to delivery systems having an ultrasound probe for improved imaging and a curved needle for ablation treatment, and methods for using the same.

BACKGROUND OF THE INVENTION

Treatment of the female reproductive tract and other conditions of dysfunctional uterine bleeding and fibroids remain with unmet clinical needs. Fibroids are benign tumors of the uterine myometria (muscle) and are the most common tumor of the female pelvis. Fibroid tumors affect up to 30% of women of childbearing age and can cause significant symptoms such as discomfort, pelvic pain, mennorhagia, pressure, anemia, compression, infertility, and miscarriage. Fibroids may be located in the myometrium (intramural), adjacent the endometrium (submucosal), or in the outer layer of the uterus (subserosal). Most common fibroids are a smooth muscle overgrowth that arise intramurally and can grow to be several centimeters in diameter.

Current treatments for fibroids include either or both pharmacological therapies and surgical interventions. Pharmacological treatments include the administration of medications such as NSAIDS, estrogen-progesterone combinations, and GnRH analogues. All medications are relatively ineffective and are palliative rather than curative.

Surgical interventions include hysterectomy (surgical removal of the uterus) and myomectomy. Surgical myomectomy, in which fibroids are removed, is an open surgical procedure requiring laparotomy and general anesthesia. Often these surgical procedures are associated with the typical surgical risks and complications along with significant blood loss and can only remove a portion of the culprit tissue.

To overcome at least some of the problems associated with open surgical procedures, laparoscopic myomectomy was pioneered in the early 1990's. However, laparoscopic myomectomy remains technically challenging, requiring laparoscopic suturing, limiting its performance to only the most skilled of laparoscopic gynecologists. Other minimally invasive treatments for uterine fibroids include hysteroscopy, uterine artery ablation, endometrial ablation, and myolysis.

While effective, hysterectomy has many undesirable side effects such as loss of fertility, open surgery, sexual dysfunction, and long recovery time. There is also significant morbidity (sepsis, hemorrhage, peritonitis, bowel and bladder injury), mortality and cost associated with hysterectomy. Hysteroscopy is the process by which a thin fiber optic camera is used to image inside the uterus and an attachment may be used to destroy tissue. Hysteroscopic resection is a surgical technique that uses a variety of devices (loops, roller balls, bipolar electrodes) to ablate or resect uterine tissue. The procedure requires the filling of the uterus with fluid for better viewing, and thus has potential side effects of fluid overload. Hysteroscopic ablation is limited by its visualization technique and thus, only appropriate for fibroids which are submucosal and/or protrude into the uterine cavity.

Uterine artery embolization was introduced in the early 1990's and is performed through a groin incision by injecting small particles into the uterine artery to selectively block the blood supply to fibroids and refract its tissue. Complications include pelvic infection, premature menopause and severe pelvic pain. In addition, long term MRI data suggests that incomplete fibroid infarction may result in regrowth of infarcted fibroid tissue and symptomatic recurrence.

Endometrial ablation is a procedure primarily used for dysfunctional (or abnormal) uterine bleeding and may be used, at times, for management of fibroids. Endometrial ablation relies on various energy sources such as cryo, microwave and radiofrequency energy. Endometrial ablation destroys the endometrial tissue lining the uterus, and although an excellent choice for treatment of dysfunctional uterine bleeding, it does not specifically treat fibroids. This technique is also not suitable treatment of women desiring future childbearing.

Myolysis was first performed in the 1980's using lasers or radio frequency (RF) energy to coagulate tissue, denature proteins, and necrose myometrium using laparoscopic visualization. Laparoscopic myolysis can be an alternative to myomectomy, as the fibroids are coagulated and then undergo coagulative necrosis resulting in a dramatic decrease in size. As with all laparoscopic techniques, myolysis treatment is limited by the fact that it can only allow for visualization of subserosal fibroids.

Needle myolysis uses a laparoscope, percutaneous, or open technique to introduce one or more needles into a fibroid tumor under direct visual control. Radio frequency current, cryo energy, or microwave energy is then delivered between two adjacent needles (bipolar), or between a single needle and a distant dispersive electrode affixed to the thigh or back of the patient (unipolar). The aim of needle myolysis is to coagulate a significant volume of the tumor, thereby cause substantial shrinkage. The traditional technique utilizes making multiple passes through different areas of the tumor using the coagulating needle to destroy many cylindrical cores of the abnormal tissue. However, the desirability of multiple passes is diminished by the risk of adhesion formation which is thought to escalate with increasing amounts of injured uterine serosa, and by the operative time and skill required. Myolysis can be an alternative to myomectomy, as the fibroids are coagulated and then undergo coagulative necrosis resulting in a dramatic decrease in size. Myolysis is generally limited by its usage with direct visualization techniques, thus being limited to the treatment of subserosal fibroids.

To overcome the limitations of current techniques, it would be desirable to provide a minimally invasive approach to visualize and selectively eradicate fibroid tumors within the uterus. The present invention addresses these and other unmet needs.

BRIEF SUMMARY OF THE INVENTION

The present invention is directed to delivery systems, and methods using the same, having an ultrasound probe for improved imaging and a needle for ablation treatment of target tissues. In some embodiments, the needle is straight with the ultrasound probe having an ultrasound array at a distal portion. In other embodiments, the needle is a curved needle. Typically, the needle will be deployed from within a natural or created body cavity or body lumen. Exemplary body cavities include the uterus, the esophagus, the stomach, the bladder, the colon, and the like. Exemplary body lumens include the ureter, the urethra, fallopian tubes, and the like. Created body cavities include insufflated regions in the abdomen, the thoracic cavity, regions around joints (for arthroscopic procedures), and the like. The present invention will generally not find use with procedures in blood vessels or other regions of the vasculature. Thus, while the following description will be directed particularly at procedures within the uterus for detecting and treating uterine fibroids, the scope of the present invention is not intended to be so limited. In an embodiment, the target tissue is a fibroid within a female's uterus.

In an embodiment, a rigid delivery system comprises a rigid delivery shaft, an imaging core, and an interventional core. In an embodiment, the rigid shaft having a proximal end, a distal end, and an axial passage extending through the rigid shaft. The axial passage will typically extend the entire length of the shaft from the proximal to the distal end, and is open at least at the proximal end. The shaft will usually be rigid along all or a portion of its length, but in other instances may be flexible, deflectable, or steerable.

In an embodiment, the imaging core preferably comprises an ultrasound imaging insert or probe disposed within the axial passage, usually being removably disposed so that it may be removed and replaced to permit sterilization and re-use. The imaging insert will have an ultrasound array within a distal portion thereof. In an embodiment, the ultrasound array is tilted relative to a shaft axis so as to provide an enhanced field of view, as discussed in more detail below. The ultrasound array may be tilted at an angle in a range from about 7 degrees to about 15 degrees, preferably in a range from about 7 degrees to about 10 degrees. It will be appreciated that the interventional core may be adapted for any conventional form of medical imaging, such as optical coherence tomographic imaging, direct optic visualization, and as such is not limited by ultrasonic imaging.

In an embodiment, the ultrasound imaging insert further comprises a flat viewing window disposed over the ultrasound array at the distal portion. The distal end of the rigid shaft may comprise a mechanical alignment feature, as for example, a flat viewing surface for axial or rotational orientation of the ultrasound imaging insert within the shaft. The flat viewing surface will be visually transparent to permit imaging from within the axial passage by the imaging insert. It will be appreciated, however, that the transparent visualization window which aids in physical alignment does not have to be visually transparent for ultrasound. For example, at least a portion of the flat viewing surface may be composed of an ultrasonically translucent material to permit ultrasonic imaging though the surface of the shaft. Further, the re-usable ultrasound imaging insert may be acoustically coupled to the outer delivery shaft to ensure that the ultrasound energy effectively passes from one component to the other. Ultrasonic acoustic coupling may be accomplished in several ways by one or a combination of means, including a compliant material (e.g., pad, sheet, etc.), fluid (e.g., water, oil, etc.), gel, or close mechanical contact between the rigid shaft and ultrasound imaging insert.

In an embodiment, the rigid delivery shaft preferably has a deflectable or fixed pre-shaped or pre-angled distal end. The delivery shaft distal end may be deflected or bent at an angle in a range from about 0 degrees to about 80 degrees relative to the shaft axis, preferably in a range from about 10 degrees to about 25 degrees. The ultrasound imaging insert will usually be flexible (and in some instances deflectable or steerable) so that the distal portion of the ultrasound imaging insert is conformable or bendable to the same angle as the shaft deflectable distal end. The cumulative effect of array tilting and shaft bending advantageously provides an enhanced viewing angle of the ultrasound imaging insert, which is in a range from about 7 degrees (i.e., angle due to tilted ultrasound array) to about 90 degrees relative to the shaft axis.

In a preferred embodiment, the viewing angle is about 20 degrees, wherein the array tilting and shaft bending are at about 10 degrees respectively. It will be appreciated that several geometries of array tilting and shaft bending may be configured so as to provide the desired viewing angle (e.g., distally forward direction, side-viewing or lateral direction), as for example, viewing of the end within the uterus (e.g., cornua and fundus).

In an embodiment, the interventional core preferably comprises a curved needle coupled to the rigid shaft via a needle guide. Significantly, an angle of needle curvature is dependent upon (e.g., inversely proportional to) the ultrasound array tilt and the shaft bend. For example, an increase in an angle of array tilting or shaft bending decreases an angle of needle curvature. This in turn provides several significant advantages such as allowing a treating physician or medical facility to selectively choose an appropriate needle curvature based upon such indications (e.g., variability in needle curvature). Further, a decrease in the angle of needle curvature provides for enhanced pushability, deployability, and/or penetrability characteristics as well as simplified manufacturing processes. The angle of needle curvature may be in a range from about 0 degrees to about 80 degrees relative to an axis, preferably the angle is about 70 degrees when the viewing angle is about 20 degrees. The curved needle generally comprises a two-piece construction comprising an elongate hollow body and a solid distal tip. The solid tip may comprise an asymmetric or offset trocar tip. For example, the tip may comprise a plurality of beveled edges offset at a variety of angles. It will be appreciated that the needle may take on a variety of geometries in accordance with the intended use.

In an embodiment, the needle extends adjacent an exterior surface of the rigid delivery shaft. In an embodiment, the needle is disposed within a needle guide which extends along an exterior of the rigid shaft. The curved needle may be removably and replaceably disposed within the guide passage. The guide passage will typically extend approximately the entire length of the shaft and be open at least at the distal end so as to allow the needle to be reciprocatably deployed and penetrated into adjacent solid tissue. In an embodiment, the needle has a hollow body and a solid distal tip formed from conductive material. The needle, optionally, may be covered, at least along a distal portion of the needle body, with a sheath. In an embodiment, the sheath is retractable such that the needle distal tip is extendable from a sheath's distal end thereby adjusting the length of the exposed conductive distal tip. In an embodiment, the sheath is formed from non-conductive material such as parylene.

In an embodiment, the curved needle and needle guide have a flattened oval shape that has a wideness that is greater than a thickness. This oval cross sectional shape is intended to inhibit lateral deflection during deployment or penetration of the needle. The needle is configured to deliver to the target site radio frequency energy (or other ablative energy such as, but not limited to, electromagnetic energy including microwave, resistive heating, cryogenic) generated at a relatively low power and for relatively a short duration of active treatment time.

In an embodiment, a delivery system includes a shaft, an imaging core, and an interventional core. The delivery shaft has a proximal end, an angled distal tip, and an axial passage therethrough. The imaging core comprises an ultrasound imaging insert disposed within the axial passage. The imaging insert has an ultrasound array within a distal portion thereof, wherein the ultrasound array is tilted relative to a shaft axis. The interventional core comprises a curved ablation needle coupled to the shaft. An angle of needle curvature may be inversely proportional to the ultrasound array tilt and tip angle.

As discussed above, the geometries of the shaft, imaging insert, treatment needle, and needle guide may be varied in accordance with the intended use. The delivery shaft, ultrasound imaging insert, treatment needle, and/or needle guide may be integrally formed or fixed with respect to one another or preferably comprise separate, interchangeable modular components that are coupleable to one another to permit selective sterilization or re-use, and to permit the system to be configured individually for patients having different anatomies and needs. For example, a sterilizable and re-usable ultrasound insert may be removably positioned within a disposable shaft.

The target site undergoing treatment may be any target site which may benefit from the treatment devices and methods according to the present invention. Usually the target site is a uterus within a female's body. The target site in need of treatment generally has an initial (e.g., prior to treatment) approximate diameter which is greater than about two (2) centimeters ("cm"). Usually, the target site's initial diameter ranges from about 1 to about 6 cm. Normally the initial untreated diameter is about 2 cm.

In an embodiment of methods according to the present invention for visualization and ablation of fibroid tissues needing treatment within a patient's body include providing a visualization and ablation system according the device and system embodiments described herein. In an embodiment, the method comprises inserting a rigid shaft having a proximal end, a distal end, and an axial passage therethrough within a uterus. The distal end of the rigid shaft may then be selectively deflected. An ultrasound imaging insert may then be loaded within the axial passage prior to, concurrent with, or subsequent to shaft insertion, wherein a distal portion of the insert conforms to the deflected shaft distal end. Loading may further involve axially or rotationally aligning the ultrasound imaging insert within the rigid shaft. A needle curvature is then selected by the physician or medical facility from a plurality of needles (i.e., at least two or more) having different curvatures based on at least an angle of the deflected shaft distal end. The selected curved needle is then loaded along the rigid shaft. Under the guidance of the imaging system, the needle is inserted into the tissue site. The RF generator is set to deliver and/or maintain a target temperature at the target site for a treatment period.

In an embodiment, the ultrasound array may be tilted or inclined within the distal portion of the insert, wherein selecting the needle curvature further comprises accounting for the ultrasound array tilt. As described above, the ultrasound array is preferably tilted at an angle in a range from about 7 degrees to about 10 degrees relative to a shaft axis. Deflecting will typically comprise pulling a pull or tensioning wire coupled to the shaft distal end in a proximal direction. Deflection occurs at an angle in a range from about 0 degrees to about 80 degrees relative to the shaft axis, wherein the needle curvature is in a range from about 0 degrees to about 90 degrees (i.e., in the case of a non-tilted ultrasound array) relative to an axis. The method further comprises imaging the uterus with a viewing angle of the ultrasound array in a range from about 0 degrees to about 90 degrees (i.e., in the case of a straight needle) relative to the shaft axis, wherein the viewing angle is based upon the deflected shaft distal end and the tilted ultrasound array. It will be appreciated that torquing and/or rotating the rigid device in addition to tip deflection and ultrasound tilt will allow a physician to obtain the desired viewing plane.

In some embodiments, methods further include ablating a uterine fibroid within the uterus with the selected curved needle. In those cases, the needle may be a radiofrequency (RF) electrode, a microwave antenna, a cryogenic probe, or other energy delivery or mediating element intended for ablating or otherwise treating tissue. The distal tip of the needle will usually be adapted so that it will self-penetrate into the tissue as it is advanced from the needle guide. The direction of advancement will be coordinated with the imaging field of the ultrasound insert so that the penetration of the curved needle can be viewed by the physician, usually in real time. Further, an electrolyte (e.g., saline) or other agent may be infused within the uterus prior to or concurrently with fibroid ablation so as to enhance the therapeutic effect provided by the treatment needle. This is preferably accomplished by providing at least one or more (e.g., two, three, four, five, etc.) infusion holes or apertures on the needle body. In still other cases, the needle could be a hollow core needle intended for sampling, biopsy, otherwise performing a diagnostic procedure.

In an embodiment, the power and temperature are generated by a radio frequency energy generator. The radio frequency energy generator is generally configured to deliver energy at a power from about 1 to about 50 watts ("W"), generally from about 1 to about 40 W, usually from about 20 to about 40 W, and normally about 30 W. The radio frequency energy generator is further configured to provide a target temperature at the target site ranging from about 50 to about 110 degrees Celsius (".degree. C."), usually from about 60 to about 100.degree. C., normally about 90.degree. C. In an embodiment, the needle's conductive tip is at approximately body temperature as it is initially disposed within the patient's body.

In an embodiment, the target site is treated for a period of time ranging from about 1 to about 10 minutes, generally from about 1 to about 8 minutes, usually from about 3 to about 8 minutes, normally about 6 minutes.

In an embodiment, at least one fluid lumen extends along the rigid shaft for delivering fluids to a distal portion of the delivery system. The at least one fluid lumen may be configured for delivery of any one or more of fluids such as those for enhancing acoustic coupling between the ultrasound imaging insert and the target site, contrasting dyes, therapeutic agents, and the like. In an embodiment, the at least one fluid lumen includes acoustic coupling lumens including an internal lumen extending along the axial passage and terminating at an internal port within its distal end and an external lumen extending along the axial passage and terminating at an external port in fluid communication with the outside of the axial lumen. In an embodiment, the external lumen is formed by an external hollow tubular body extending along the needle guide, while the internal lumen is formed by an internal hollow tubular body extending along the underside of the axial hollow tubular body forming the axial passage. It should be appreciated, however, that the external and internal fluid lumens may be oriented in any other suitable location along the shaft. In the embodiment, as shown, the external lumen is located along the needle guide such that the fluid may exit near the ultrasound window, while the internal lumen extends along the underside of the axial hollow tubular body which forms the axial passage so as to allow the fluid to be delivered to the inner tip without trapping air inside the shaft.

In an embodiment, the present invention includes a visualization and ablation system generally having a delivery device, an ultrasound imaging probe detachable from the delivery system, a radio frequency energy generator, and an ultrasound system.

BRIEF DESCRIPTION OF THE DRAWINGS

The following drawings should be read with reference to the detailed description. Like numbers in different drawings refer to like elements. The drawings illustratively depict embodiments including features of the present invention. The drawings are not necessarily drawing to scale and are not intended to limit the scope of the invention.

FIGS. 1A through 1E illustrate an exemplary embodiment of a delivery system embodying features of the present invention and having an inclined ultrasound array for improved imaging and a curved needle for ablation treatment.

FIGS. 2A through 2D illustrate exploded views of the distal portion of the ultrasound imaging insert of FIG. 1A in a straight configuration.

FIGS. 3A through 3D illustrate exploded views of the distal portion of the ultrasound imaging insert of FIG. 1A in a bent configuration.

DETAILED DESCRIPTION OF THE INVENTION

Figure 1D:
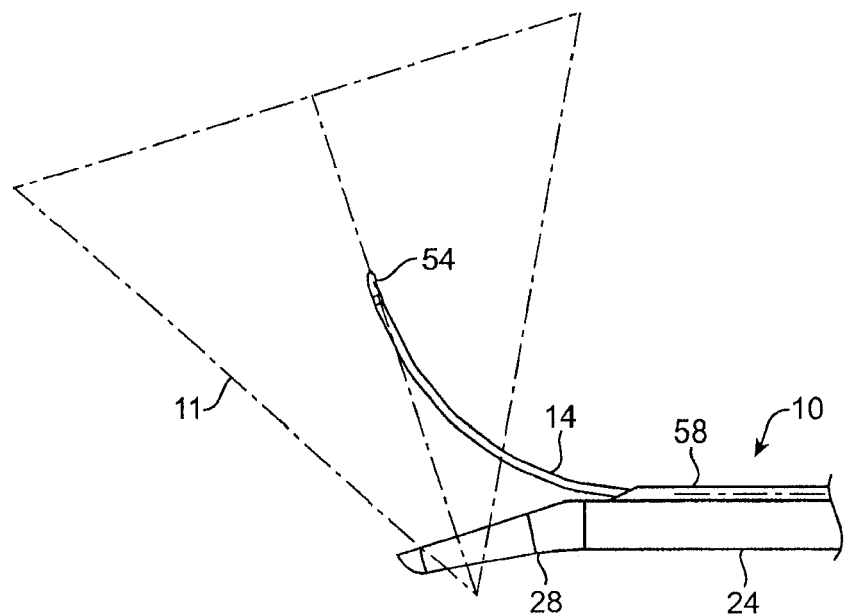
Figure 1E:
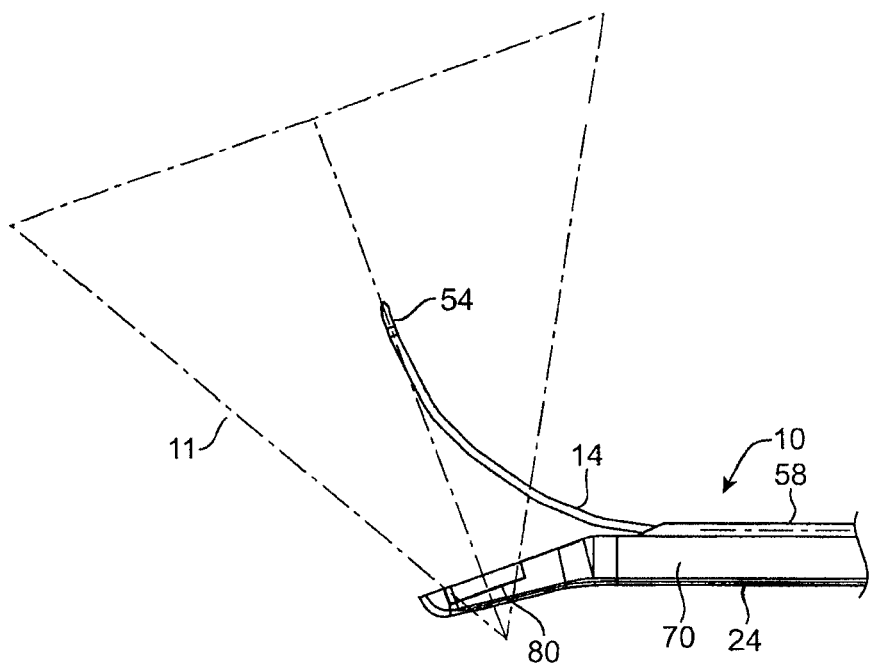

Referring to FIGS. 1A through 1C, an exemplary delivery system 10 embodying features of the present invention is shown having a shaft inclined viewing window 12 for improved imaging and a curved needle 14 for ablation treatment of a target site 16 such as fibroid tissues 18 (FIG. 5E) within a female's reproductive system. The delivery system 10 includes a system distal end 20, a system proximal end 22, and a rigid delivery shaft 24. Delivery shaft 24 includes a shaft distal end 26 with a bent or deflectable shaft distal tip 28, a shaft proximal end 30, and an axial passage 32 extending longitudinally through at least a portion of the delivery shaft 24. A handle 40 with handle proximal and distal ends 42 and 44, is attachable to the shaft proximal end 30. The handle 40 further includes a longitudinally movable slider 45 for enabling the advancement and retraction of the needle 14 to and from within a needle guide 58.

Figure 4A:
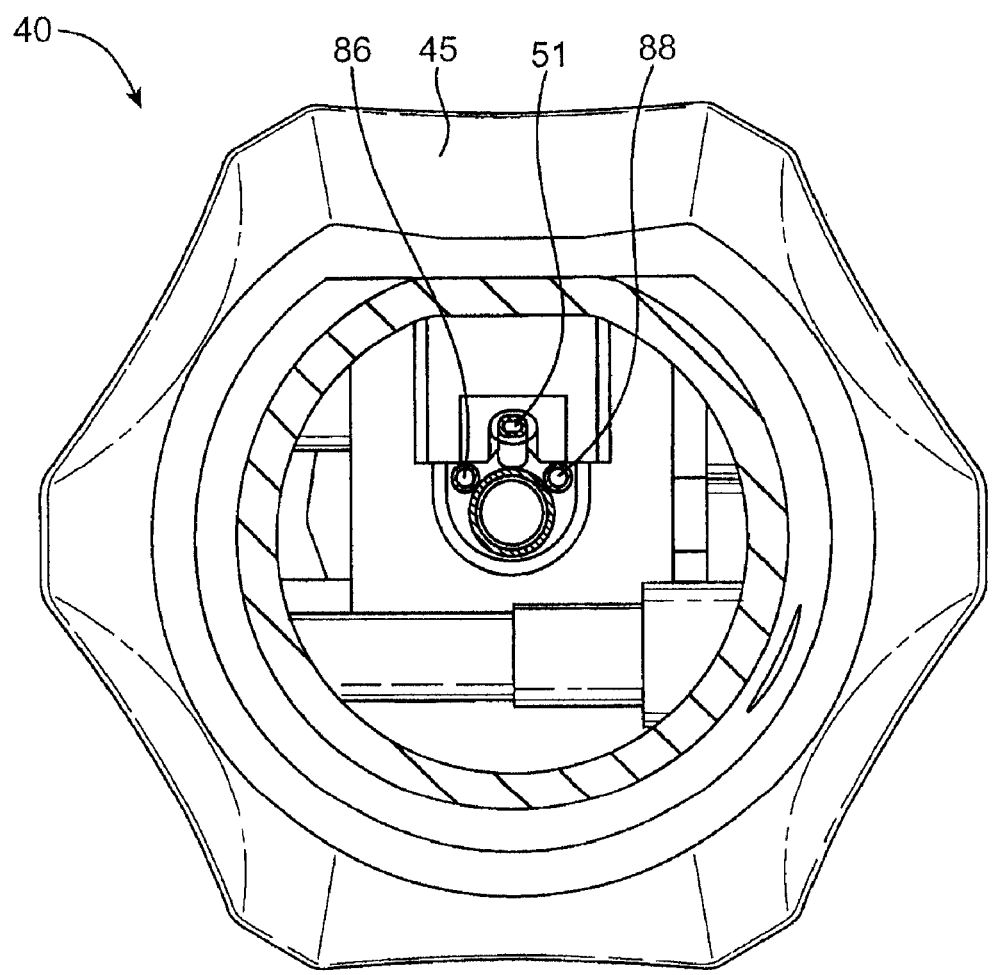
FIGS. 4A through 4E illustrate cross-sectional views of the embodiments of exemplary delivery system of FIGS. 1A through 1C taken along their respective lines.
Figure 4B:
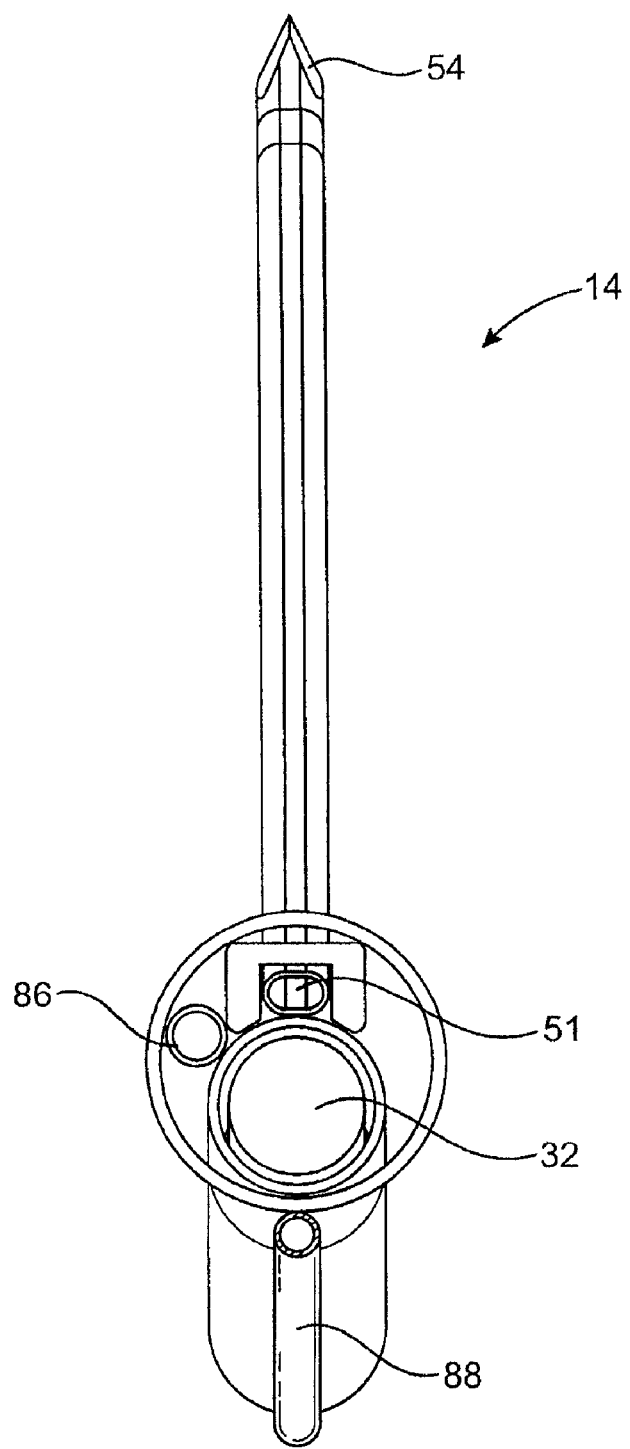
Figure 4C:
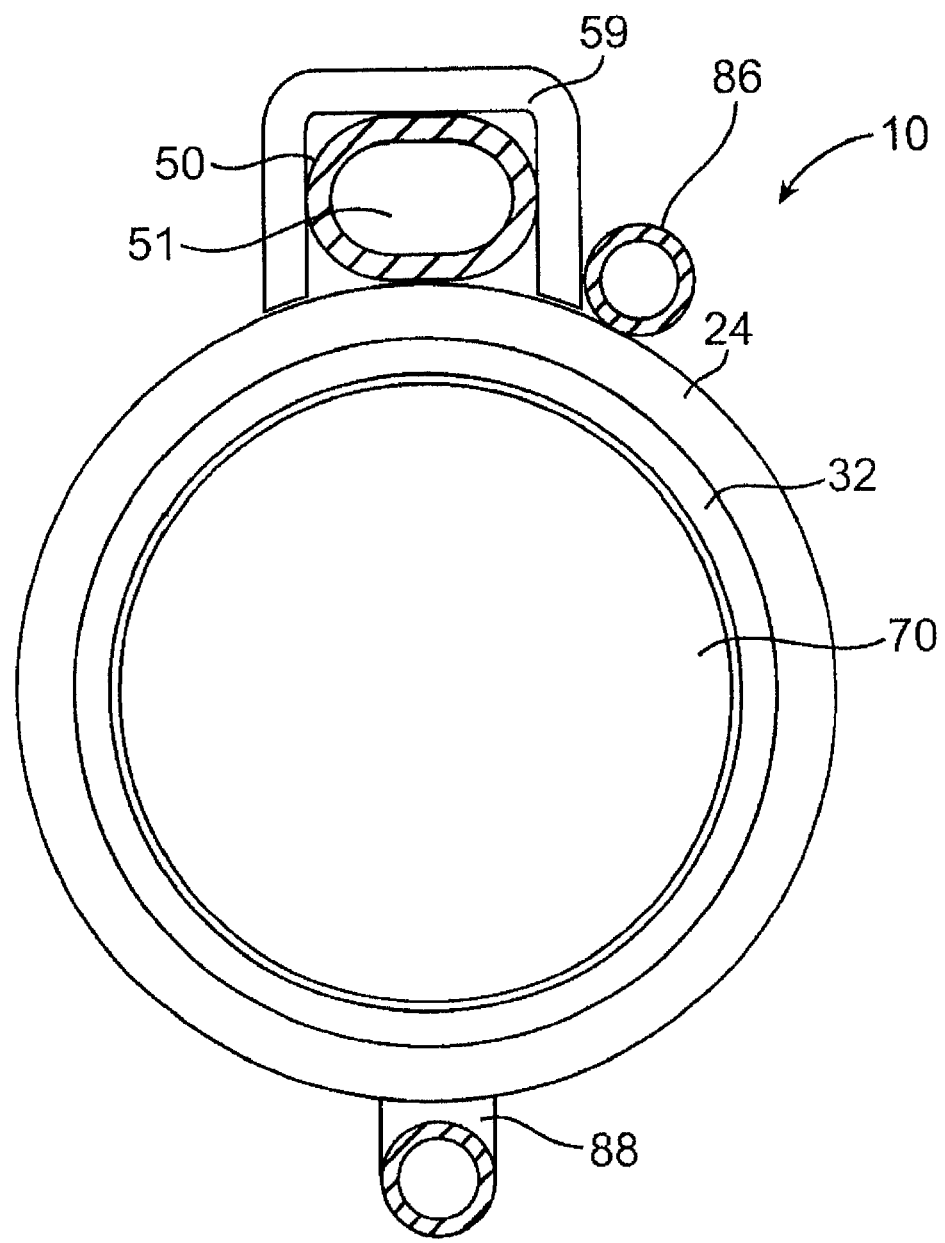
Figure 4D:
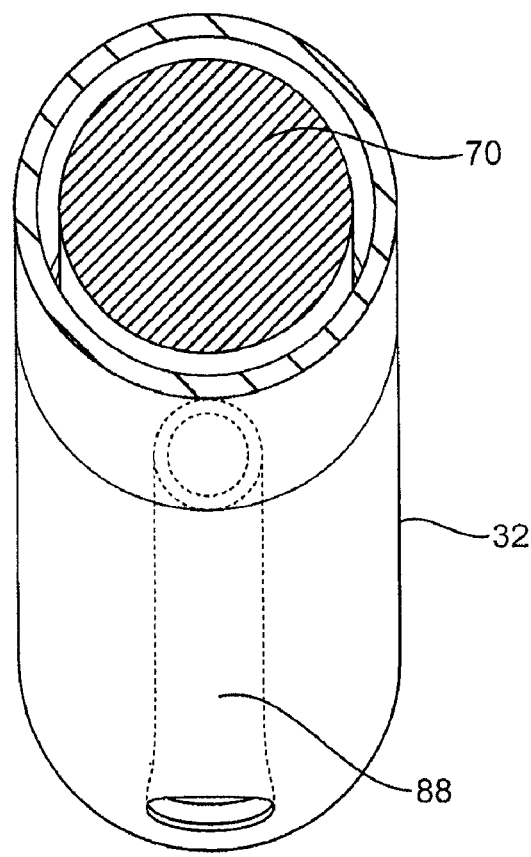
Figure 4E:
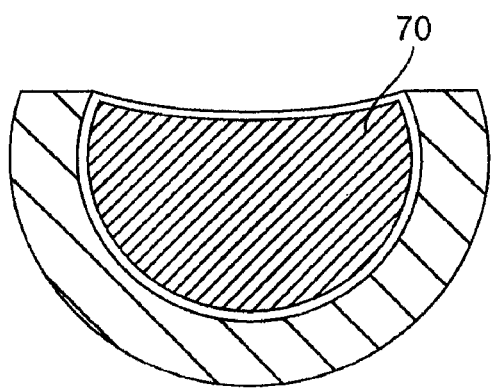

The curved needle 14 has a needle body 50 with a shaped needle distal end 52 and a solid needle distal tip 54, as best seen in FIGS. 1B-1E and 4A-E. Needle 14 is configured to deliver, to the target site 16 including fibroid 18 (as shown in FIG. 5E), radio frequency energy generated at a relatively low power and for relatively a short duration of time from an ablative energy generator 400 (such as, but not limited to, electromagnetic energy including microwave, resistive heating, cryogenic) including a radio frequency (RF) energy generator 410, as shown in and discussed in reference to FIGS. 5A and 5E. In an embodiment, as shown, needle body 50 is a hollow body forming a needle lumen 51.

Now referring back to FIGS. 1A and 1B, needle 14 is disposed adjacent the exterior of the shaft 24 within the needle guide 58. Needle guide 58 includes a guide passage 59 and is attachable to the shaft by way of adhesive, or other means such as laser welding, shrink tubing, and the like. Needle 14, as best seen in FIGS. 1B, 4B, and 5C, may include one or more needle apertures 60. As shown, the needle 14 includes two needle aperture 60A and 60B. The most distal aperture 60A exposes the distal end of a thermocouple pair 59a and 59b as shown in FIG. 6C. The proximal aperture 60B may be used for delivery of various therapeutic and/or imaging enhancement fluids and contrasting agents/dyes to the target site 16 and fibroid 18. In the embodiment shown, contrasting dye runs within the lumen 51 of the hollow needle body. As can be seen from FIG. 6C, the thermocouple pair 59a and 59b are disposed within the lumen 51 for monitoring the temperature at the target site 16, while the annular space around the thermocouples within lumen 51 is usable for delivery of dyes.

The shaft axial passage 32 is configured for removably and replaceably receiving and housing an ultrasound imaging insert 70. A sealing element 72 may be provided between the ultrasound imaging insert 70 and the shaft handle 40 to provide sufficient sealing around the imaging insert 70 at a proximal end.

The ultrasound imaging insert 70 as shown in FIG. 1B, and as further described below, comprises an insert flexible shaft 74, an insert proximal end 76, an insert distal end 78, an ultrasound array 80, and an insert flat viewing window 82 disposed at the insert distal end 78. The ultrasound array 80 is viewable from the shaft inclined viewing window 12. The shaft viewing window may be used for axial and/or rotational orientation of the ultrasound imaging insert 70 within the delivery system shaft 24. A simplified illustration of the delivery shaft 24 as shown in FIG. 1D carries the ultrasound imaging insert 70 within its axial passage 32. A viewing plane 11 provided by the tilted and bent ultrasound array 80 is further illustrated.

Figure 2A:
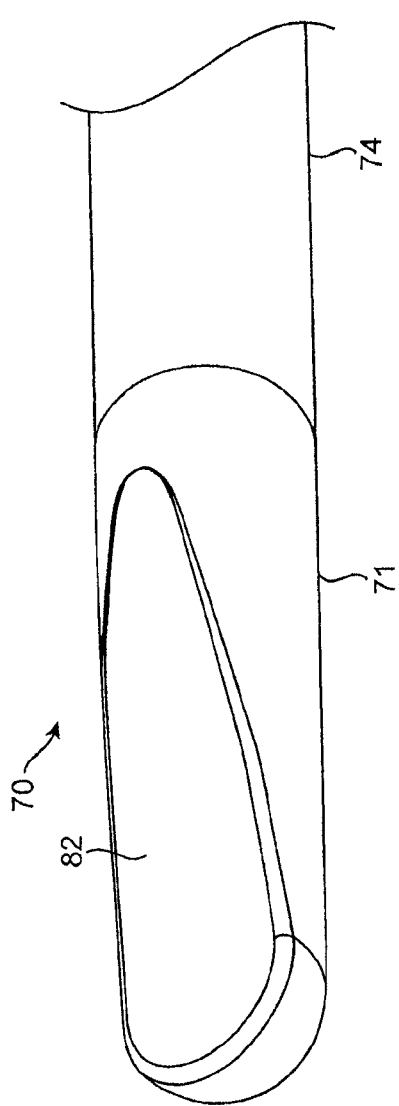
Figure 2B:
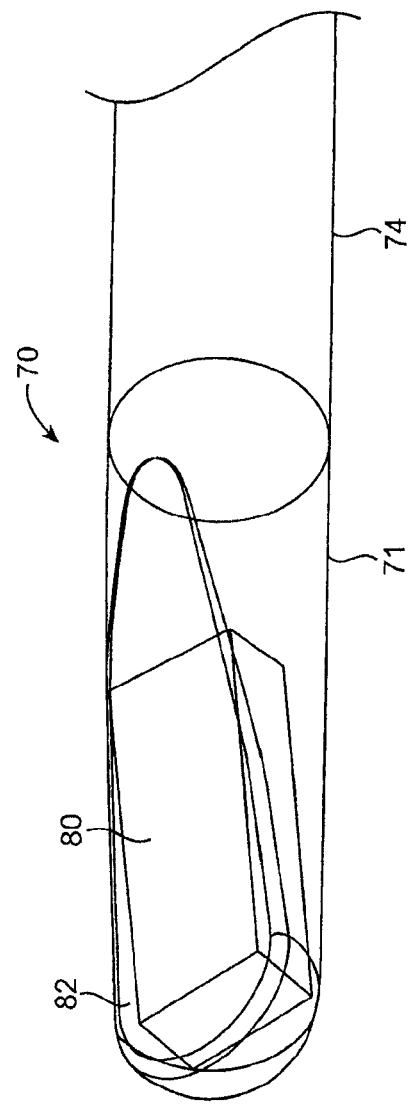

Referring now to FIGS. 2A through 2D, exploded views of a distal portion 71 of the ultrasound imaging insert 70 are illustrated. FIGS. 2A and 2C show isometric and side views respectively of the ultrasound imaging insert 70 in a straight position prior to insertion into the axial passage 32 of the delivery shaft 24, as will be described in more detail below. The ultrasound imaging insert 70 comprises a flexible shaft 74 and includes an ultrasound array 80 and a flat viewing window 82 within the distal portion 71. FIGS. 2B and 2D illustrate transparent isometric and side views respectively of the ultrasound imaging insert 70, wherein the ultrasound array 80 is shown tilted relative to a shaft axis 39. Preferably, the ultrasound array 80 is tilted or inclined at an angle α in a range from about 7 degrees to about 15 degrees. It will be appreciated that the angle α of inclination of the ultrasound array 80 may comprise a variety of angles (e.g., 0 degrees to about 45 degrees) as permitted by an outer diameter of the flexible shaft 74. The ultrasonic array 80 may be arranged in a phased array, for example either a linear phased array or a circumferential phased array. Alternatively, the ultrasonic imaging array 80 may comprise one or more independent elements, such as parabolic or other shaped imaging elements. In still further embodiments, the ultrasonic imaging array 80 may be arranged in a rotating mechanism to permit rotational scanning.

Referring now to FIGS. 3A through 3D, exploded views of a distal portion 71 of the ultrasound imaging insert 70 are further illustrated. FIGS. 3A and 3C show isometric and side views respectively of the ultrasound imaging insert 70 in a bent position subsequent to insertion into the axial passage 32 of the delivery shaft 24. In particular, the transparent isometric and side views of FIGS. 3B and 3D illustrate the cumulative effect of tilting the ultrasound array 80 relative to the shaft axis 39 at the angle α and bending the distal portion 71 of the ultrasound imaging insert 70. The bend angle β may be in a range from about 0 degrees to about 80 degrees relative to the shaft axis 41, preferably in a range from about 10 degrees to about 13 degrees. The bend angle β will be determined by the deflectable distal tip 28 of the delivery shaft 24 as the flexible insert 70 conforms to the deflectable distal tip 28 upon insertion within the shaft 24. The viewing angle κ of the ultrasound imaging insert 70 achieved by this cumulative effect may be in a range from about 7 degrees (i.e., angle due solely to tilted ultrasound array 12) to about 90 degrees relative to the shaft axis 40. In the illustrated embodiment, the viewing angle is about 20 degrees, wherein the array tilting is approximately 7 degrees and shaft bending is about 13 degrees.

In an embodiment, the deflectable distal tip 28 of the rigid shaft 24 may be deflected by the use of pull or tensioning wire(s) housed within the shaft 24. Deflection may occur at a true mechanical pivot or at a flexible zone at the shaft distal end 26. When the delivery shaft 24 is deflectable by a user, various needles 14 may be used to match the amount of deflection provided by the distal tip 28 as well as the amount of tilt provided by the ultrasound array 80. Hence, the needle guide 58 will typically be empty until the distal end 26 of the shaft 24 is deflected. For example, the shaft 24 may be inserted in a straight configuration. The distal tip 28 may then be deflected until a target anatomy is identified. A needle 14 is then back loaded within the guide passage 58 that corresponds to the amount of the deflection.

The delivery system 10, as shown in various FIGS. 1 and 2, at the device proximal end 22, includes a plurality of fluid inlet ports 100 in fluidic communication with various portions of the delivery system shaft 24, needle 14, and/or imaging insert 70. In an embodiment, features of which are shown in FIGS. 1A and 2A, system 10, includes fluid inlet ports 102, 104, and 106. Fluid inlet ports 100 (including 102, 104, and 106) are configured to direct various fluids to a distal portion 23 of the delivery system 10. By way of example, fluid inlet port 102 is configured to deliver dyes to at least one of the needle apertures 60, such as aperture 60B at the needle distal end 52; while fluid inlet ports 104 and 106 are configured, respectively, to deliver acoustic coupling fluids through external and internal axial lumens 86 and 88 disposed along axial passage 32 to a shaft external fluid outlet port 90 and a shaft internal fluid outlet port 92 at the shaft distal end 26. Same or different fluid ports, such as fluid port 102, may be further utilized to deliver other fluids such as therapeutic agents to any of the other outlet ports or apertures. Optionally, additional apertures may be provided at desired locations along lumen 51 of the hollow needle body 50.

The shaft 24 of the present invention, as described herein, may serve several functions including delivering ultrasound, diagnostic, and/or interventional treatments, bending of the ultrasound insert via the deflectable distal tip, and/or providing a sterile barrier between the ultrasound and/or interventional components. As shown in FIG. 1B, the delivery shaft 24 carries the ultrasound imaging insert 70 within its axial passage 32.

Generally, the delivery system shaft 24 will have a length in a range from about 20 cm to about 40 cm and an outer diameter in a range from about 3 mm to about 10 mm, while the ultrasound imaging insert 70 will have a length in a range from about 50 cm to about 90 cm and an outer diameter in a range from about 2 mm to about 4 mm. Delivery system shaft 24 and the ultrasound imaging insert 70 may be acoustically coupled in one or more of several ways to enable the effective passage of ultrasound energy from one component to the other. For example, the ultrasound insert 70 may be placed in close mechanical contact with the shaft 24 so as to provide a dry coupling. In addition or alternatively, a thin compliant layer (e.g., pad or sheet) may be disposed between the viewing windows 82 and 12, of the ultrasound insert 70 and the shaft 24, respectively, so as to provide further interference between such components. It will be appreciated that a thinner layer may be preferred to minimize unwanted acoustic loss, index of refraction, impedance, and/or other material property effects. Alternatively, or in addition to, the shaft axial passage 32 in which the ultrasound imaging insert 70 is disposable, may be filled with a fluid (e.g., water or oil) or gel to further provide a wet coupling between the shaft and the imaging insert which may compensate for any mechanical tolerances.

Figure 5A:
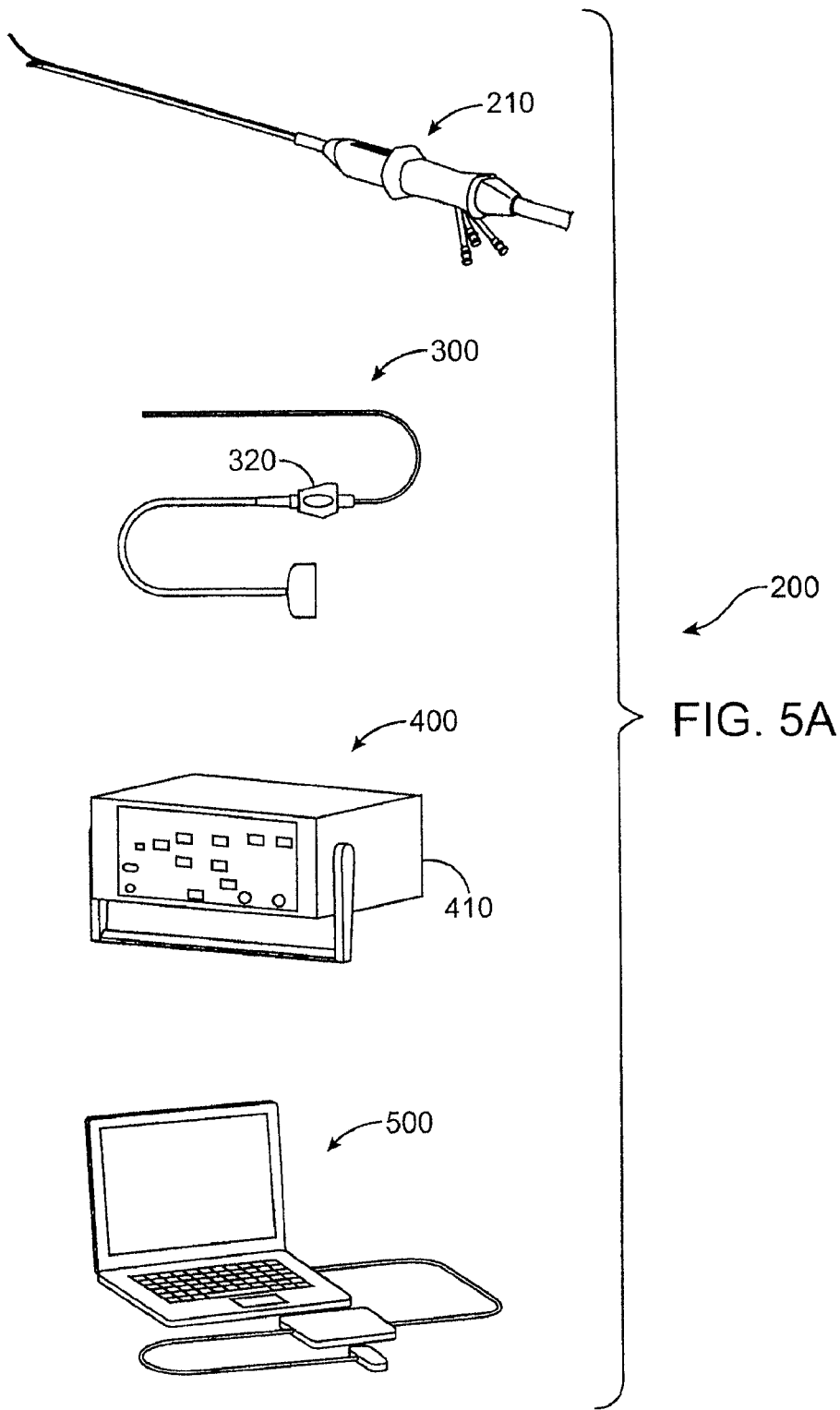
FIG. 5A illustrates a visualization and ablation system embodying features of the present invention.

Now referring to FIG. 5A, a visualization and ablation system 200 embodying features of the present invention is shown, including a delivery device 210, an ultrasound imaging probe 300 being detached from the delivery system 210, the radio frequency energy generator 410, and an ultrasound system 500. The various components of the exemplary visualization and ablation system 200 will be further described in individual detail.

Figure 5B:
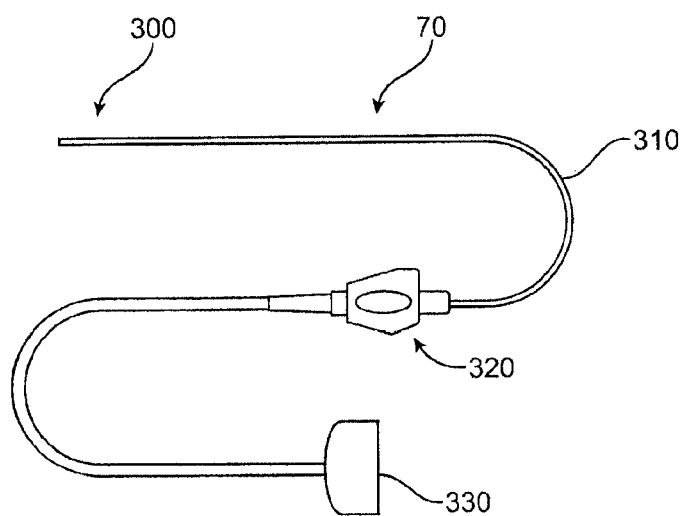
FIG. 5B illustrates features of an exemplary ultrasound probe of the visualization and ablation system of FIG. 5A.
Figure 5C:
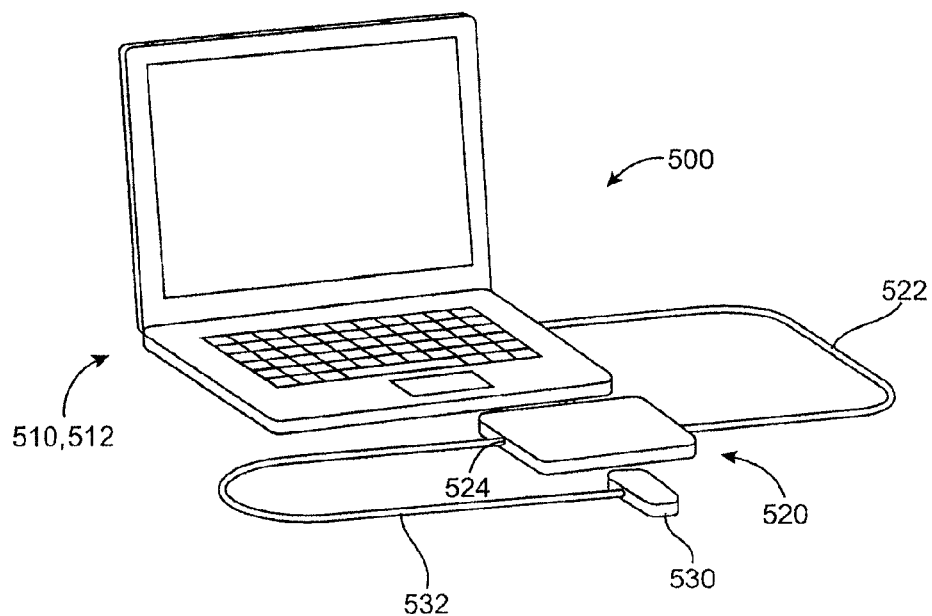
FIG. 5C illustrates features of an exemplary ultrasound system of the visualization and ablation system of FIG. 5A.

The ultrasound probe 300 embodying features of the present invention, as shown in FIG. 5B, generally includes the imaging insert 70 as generally described above, and is connectable to an imaging insert probe port 212 at the delivery system proximal end 22. The ultrasound probe 300 includes an alignment element 320 for removably engaging with the system probe port 212 of the delivery system 210 through a probe cable 310. Alignment element 320 is connectable to the ultrasound system 500 by way of an ultrasound probe attachment element 330.

The ultrasound system 500, embodying features of the present invention, as shown in FIG. 5C, generally includes a CPU 510 such as one shown operable by a laptop computer 512. The CPU 510 is connectable to a beam former 520 by way of a communications cable (such as a firewire cable) such as an ultrasound cable 522. The beam former 520 at a beam former distal end 524 is connectable to a probe attachment element 530 by a probe extension cable 532.

Figure 5D:
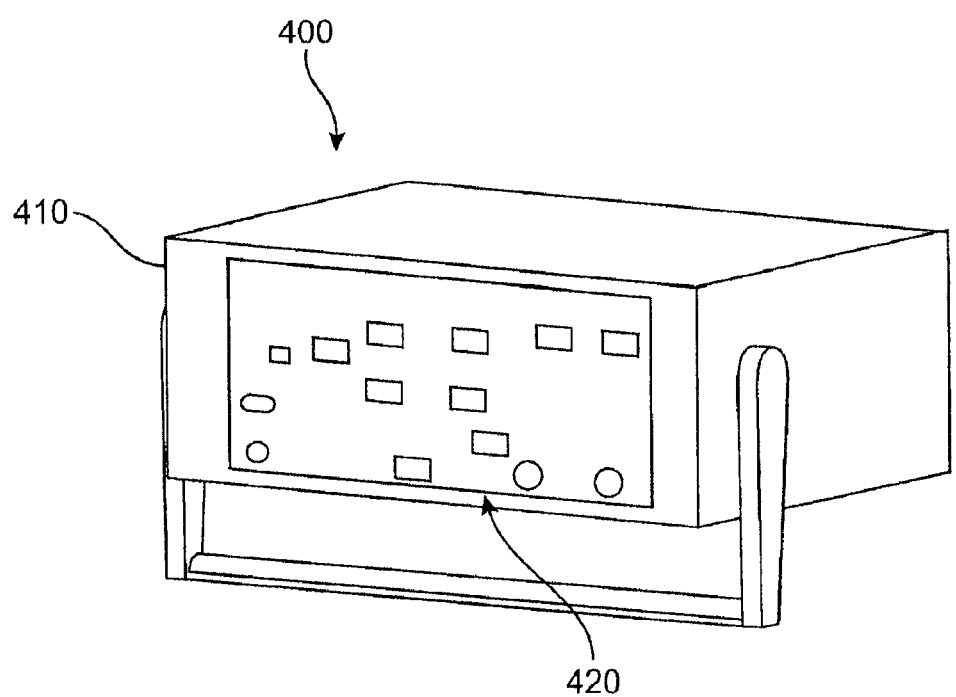
FIG. 5D illustrates features of an exemplary radio frequency energy generator of the visualization and ablation system of FIG. 5A.
Figure 5E:
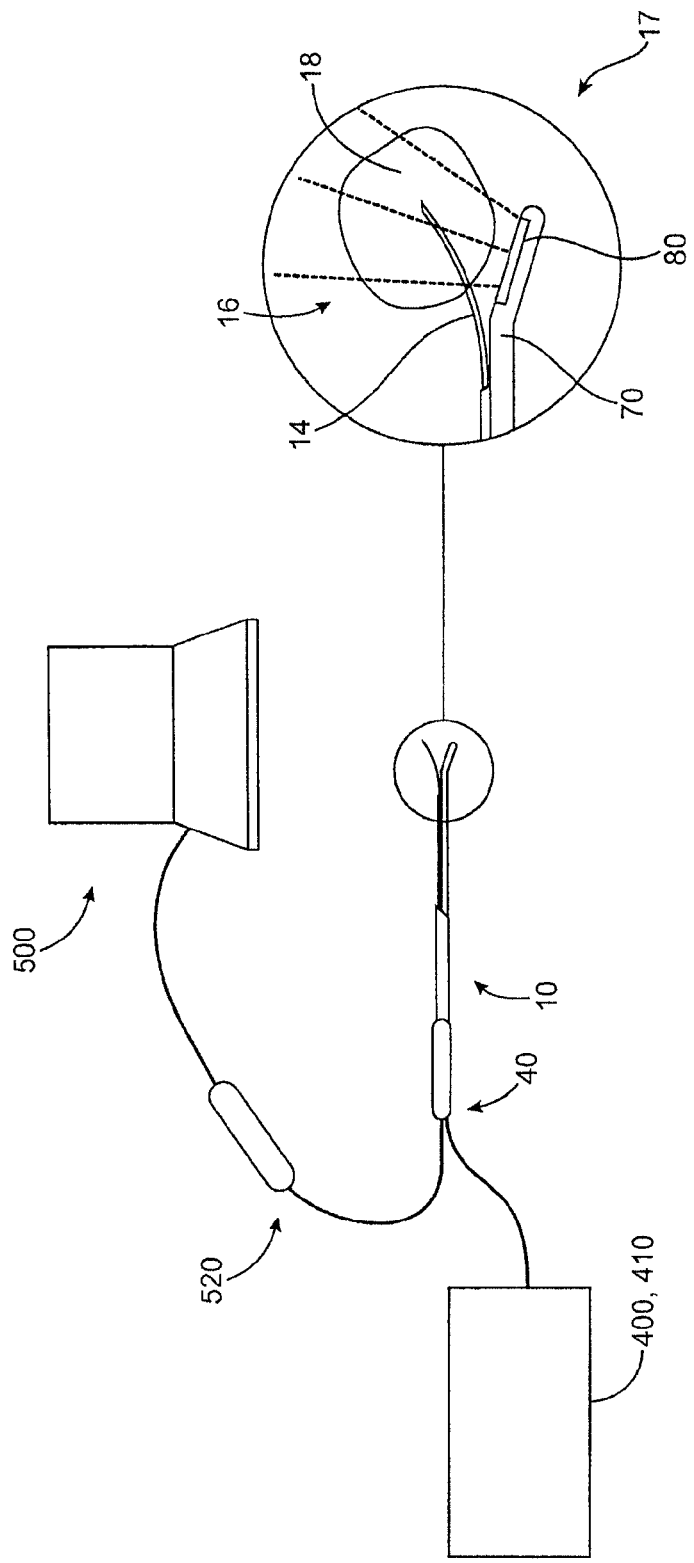
FIG. 5E illustrates the visualization and ablation system of FIG. 5A as disposed during operation within a uterus for the treatment of fibroids in accordance with the features of the present invention.

The radio frequency energy 410, embodying features of the present invention, and as shown in FIGS. 5D and 5E, is generally connectable to the delivery system 210 including needle 14, through energy outlet port 420. A suitable cable (not shown) removably connects energy outlet port 420 to a needle port 413 at the proximal end 22 of the handle 40. Radiofrequency energy is delivered from the radio frequency generator 410 to fibroid 18 at the target site 16 through needle 14 which is disposed within the needle guide 58.

Figure 6A:
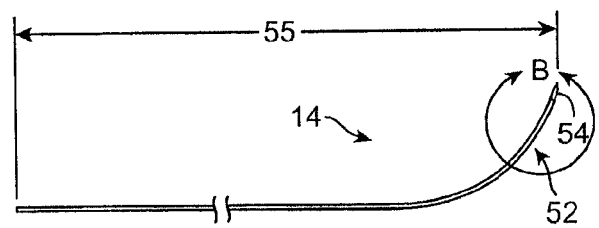
FIGS. 6A through 6C illustrate the exemplary features of an ablation needle for use with the visualization and ablation system of FIG. 5A.
Figure 6B:
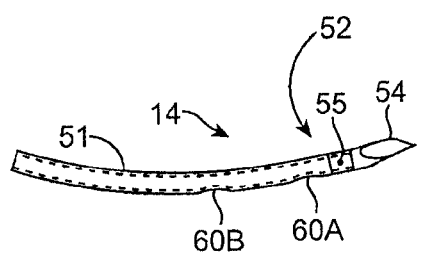
Figure 6C:
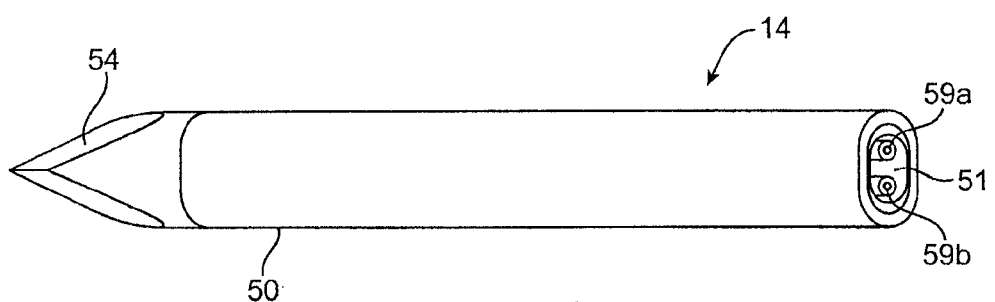

Now referring to FIGS. 6A-6C, needle 14 embodying features of the present invention, is shown disposed within the needle guide 58 which extends along the exterior of shaft 24. As further shown in cross-sectional FIGS. 7B-7D, the curved needle 14 generally comprises a two-piece construction including the elongate needle hollow body 50 with the shaped needle distal end 52 and the solid needle distal tip 54. The needle distal tip 54 may be laser welded 55 to the needle hollow body 50 as shown in FIG. 6B. The needle distal tip 54 may also be attached via alternative means, for example, adhesives or mechanical features or fits. Generally the needle hollow body 50 will have a length 55 in a range from about 20 cm to about 45 cm, an oval cross section having a thickness 57 in a range from about 0.5 mm to about 2 mm, and a wideness 59 in a range from about 1 mm to about 3 mm. In an embodiment, as shown in FIG. 7B, the oval cross section is flattened minimizing lateral deflection during deployment or penetration of the needle 14. In an embodiment, as shown in FIGS. 6B and 6C, there are two laser cut infusion apertures 60 within the tubular body 50 for the infusion of agents (e.g., electrolytes, drugs, etc., dyes/contrasts) so as to enhance either or both the visualization and therapeutic effect of the needle 14 prior to, during, or after the ablation treatment. The infusion apertures 60 may be aligned on one side of the tubular body 50. Generally, the infusion apertures have a length 63 in a range from about 0.5 mm to about 2 mm and a width 65 in a range from about 0.5 mm to about 2 mm.

Figure 7A:
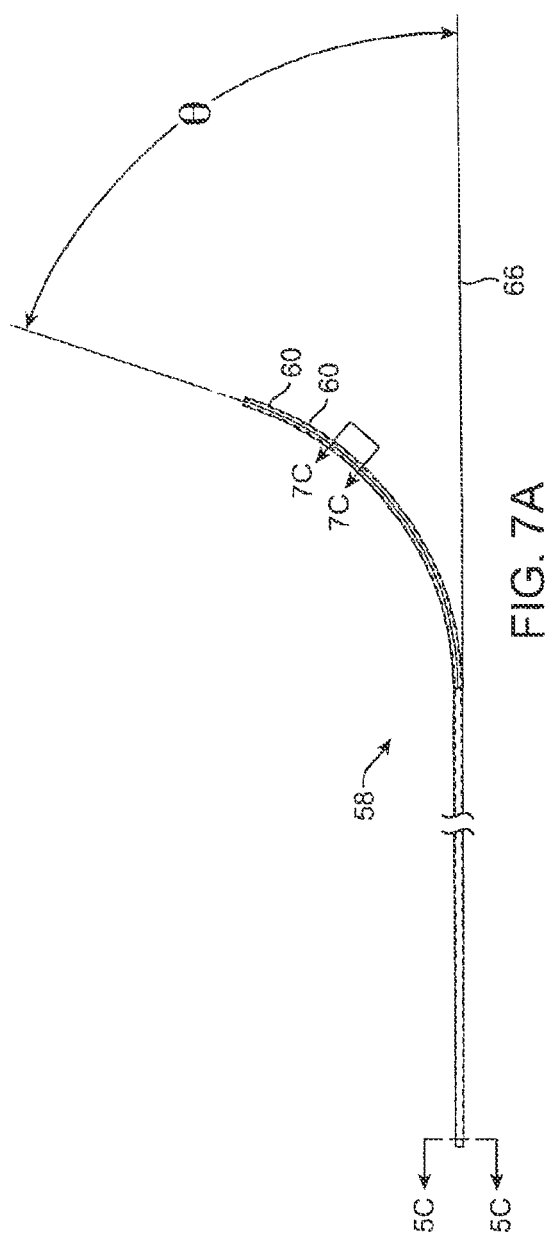
FIGS. 7A through 7D illustrate the exemplary features of an ablation needle for use with the visualization and ablation system of FIGS. 4A-4C.
Figure 7D:
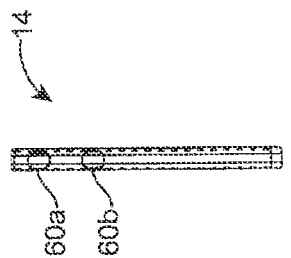
Figure 7C:
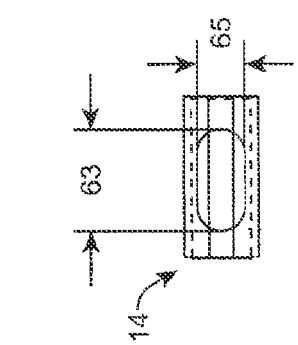
Figure 7B:
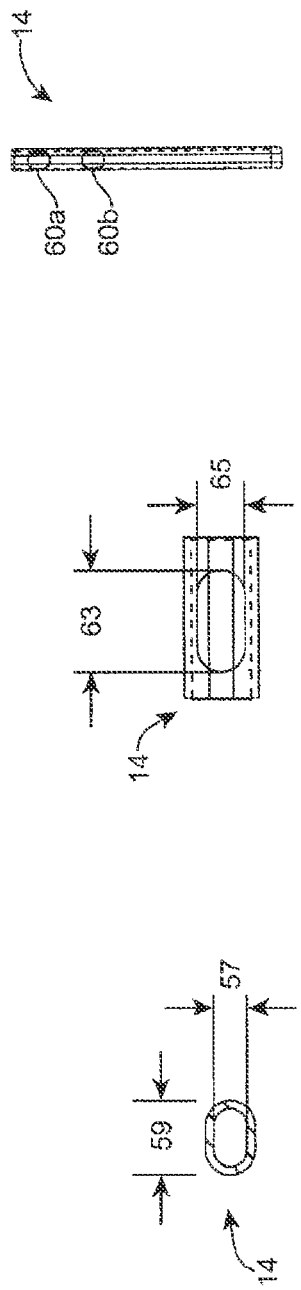

As best seen in FIG. 7A, the hollow tubular body 58 may be curved at an angle θ in a range from near 0 degrees (but greater than 0 degrees) to about 80 degrees relative to an axis 65 so as to access side/lateral fibroids. In this depiction, the angle θ is about 70 degrees. Significantly, the angle of needle curvature θ is dependent upon the ultrasound array tilt angle α and the shaft bend angle β. For example, an increase in the tilt angle α or bend angle β decreases the angle of needle curvature θ. This in turn advantageously allows a treating physician to selectively choose an appropriate needle curvature from a plurality of needles 14 (i.e., at least two or more) having different curvature angles θ. When the angle θ is 0 degrees, the needle is straight as shown, for example, in FIGS. 11A-11C.

Figure 9A:
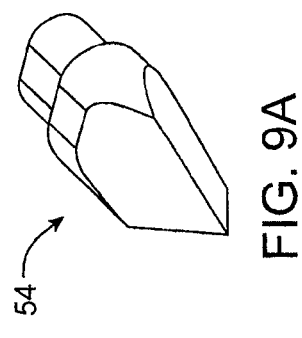
FIGS. 9A through 9E further illustrate the asymmetric solid distal tip of FIG. 6A.
Figure 9B:
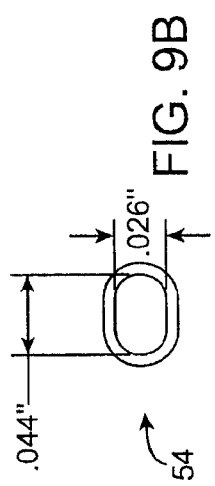
Figure 9C:
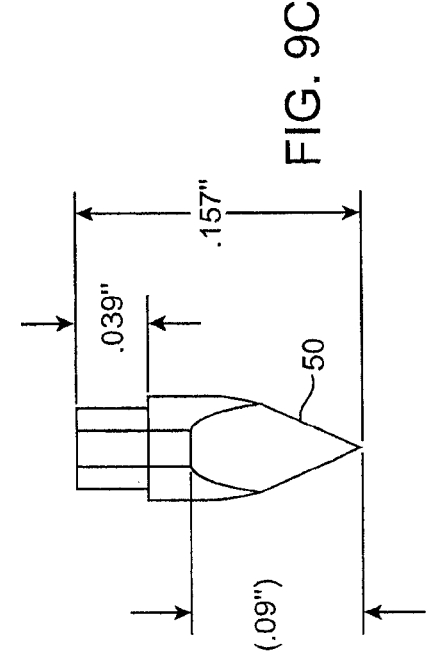
Figure 9D:
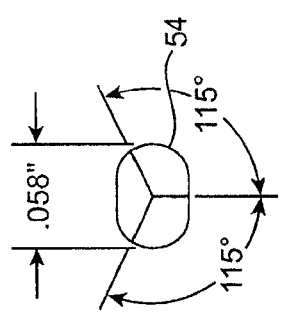
Figure 9E:
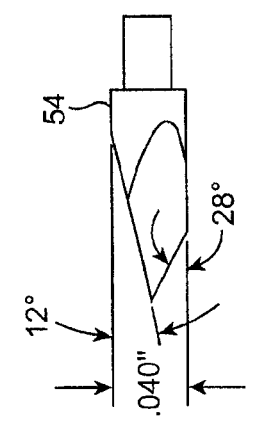

Referring now to FIGS. 9A through 9E, in an embodiment, the solid tip 54 may comprise an asymmetric or offset trocar tip. The center point of the tip 54 may be offset from a centerline of the needle to help compensate for any needle deflections due to tenacious tissue, in effect steering the needle towards the intended target even with the deflection. For example, the tip 54 may comprise a plurality of beveled edges offset at a variety of angles as illustrated in FIGS. 9D and 9E.

The needle body 50 is formed from an RF energy conductive material such as stainless steel. As will be appreciated, the solid tip 54 may comprise a variety of dimensions and shapes and is not limited to FIGS. 9A-9E. It will be further appreciated that the tip 54 need not be a separate component but may alternatively be integrally formed with the needle body 50. The needle 14, including the tip 54 and tubular body 50 may be formed from a variety of materials including stainless steel, nitinol, and the like, for transmitting ablation energy. As best seen in FIG. 1A, the handle 40 may have a needle advancement portion to reciprocatably advance or retract the needle 14 from within the needle guide 58. The needle advancement portion, as shown, is in partially advanced position for complete deployment of the needle 14. The needle guide 58 will further have an oval cross section similar to that of the needle 14, with a thickness in a range from about 0.5 mm to about 2 mm and a wideness in a range from about 1 mm to about 3 mm. The flattened guide 58 and flattened needle 14 as shown in FIG. 4C are intended to minimize lateral deflection during deployment or penetration of the needle 14 into the tissue.

Figure 8A:
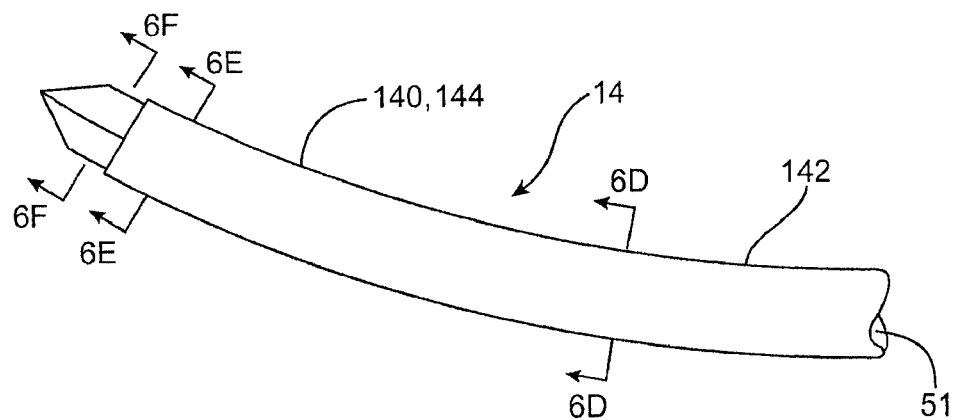
FIG. 8A illustrates an exemplary ablation needle for use with the visualization and ablation system of FIG. 5A and including an insulating material such as a retractable sheath.
Figure 8B:
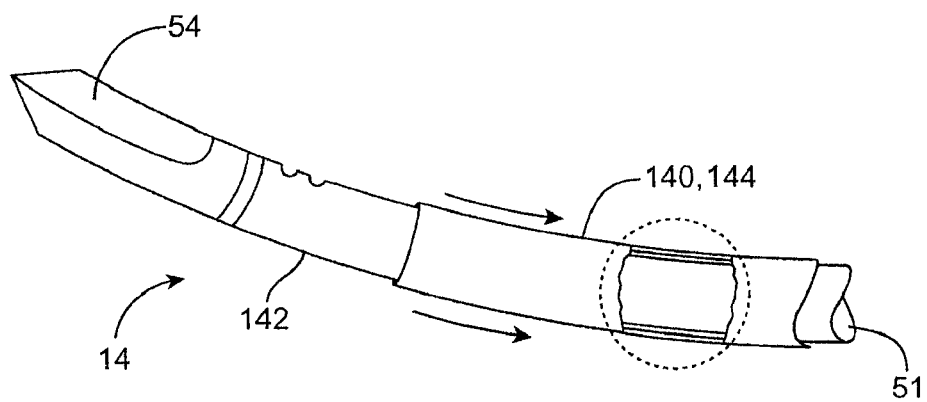
FIGS. 8B through 8C illustrate the needle of FIG. 8A with the retractable sheath in a retracted position.
Figure 8C:
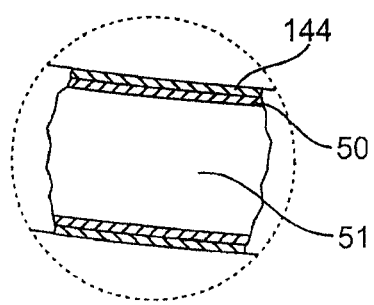
Figure 8D:
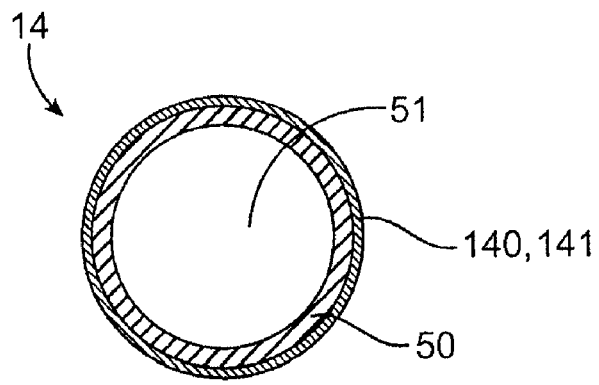
FIGS. 8D through 8F are cross-sectional views of the needle of FIG. 8A taken along lines 8D-8D, 8E-8E, and 8F-8F.
Figure 8E:
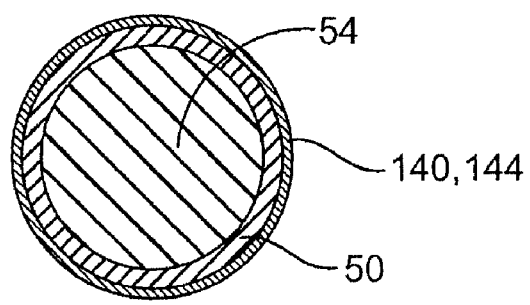
Figure 8F:
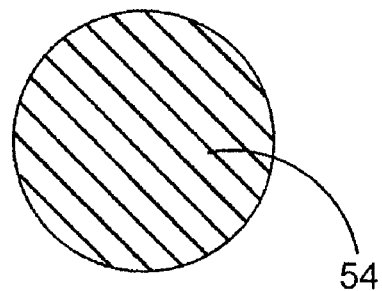

In an embodiment, as shown in FIGS. 8A-8C, an insulating material 140 extends longitudinally along at least an exterior portion 142 of the needle 14 terminating proximal to the conductive needle distal tip 54. In an embodiment, features of which are shown in FIGS. 8D-8E, the insulating material 140 forms a retractable sheath 144. The conductive needle distal tip 54 is extendable from a distal end 146 of the retractable sheath 144. The proximal retraction of the sheath 144 may be used to selectively control the length of the needle distal tip 54. As shown, the needle distal tip 54 is in a configuration distally extended from the distal end 146 of the retracted sheath 144.

The insulating sheath 140 may be formed from one or more suitable insulating material such as polyester shrink tubing, and parylene coating such as parylene C. Generally, the length of the conductive distal tip 54 ranges from about 1 to about 4 cm, usually from about 2 to about 3 cm, normally about 2 cm. In an embodiment, the conductive distal end is a T-type active electrode.

Now referring back to FIGS. 5D-E, the radio frequency energy generator 410 is configured to deliver power to the fibroid 18 at the target site 16, in a an amount ranging from about 1 to about 50 W, generally from about 10 to about 40

W, usually from about 20 to about 40 W, normally about 30 W. In an embodiment, the radio frequency energy generator 410 is configured to deliver and/or maintain a target temperature to the target site 16 ranging from about 50 to about 110.degree. C., usually from about 60 to about 100.degree. C., normally about 90.degree. C.

The target site 16, such as fibroid 18, generally has an initial untreated diameter greater than about 2 cm, usually from about 1 to about 6 cm, normally about 2 cm. During the treatment of the fibroid 18, the needle 14 may be inserted one or more times into the tissue as may be necessary. In an embodiment, the needle distal tip 54, may be deployed into the tissue, up to 3 cm as measured from the distal end of the of the delivery device 10. During the treatment, the deployed length of the needle penetrating the tissue is visualized through the ultrasound imaging system 500.

By way of operation, in an embodiment, the deflectable distal tip 26 of the rigid shaft 24 may be deflected by the use of pull or tensioning wire(s) housed within the shaft 24. In another embodiment, the distal tip may have pre-determined deflection as compared to a longitudinal axis at a proximal portion of the device. Deflection may occur at a true mechanical pivot or at a flexible zone at the shaft distal end. When the delivery shaft 24 is deflectable by a user, various needles 14 may be used to match the amount of deflection provided by the distal tip 26 as well as the amount of tilt provided by the ultrasound array 80. Hence, the needle guide 58 may be empty until the distal end 26 of the shaft 24 is deflected. For example, the shaft 24 may be inserted in a straight configuration. The distal tip 26 may then be deflected until a target anatomy is identified. A needle 14 is then back loaded within the guide passage 70 that corresponds to the amount of the deflection. Alternatively, the needle may be pre-loaded in the shaft to provide a sterile and convenient delivery device to the user.

In exemplary embodiments, the therapeutic needle 14 advancement from the guide 58 via needle advancement portion on the shaft handle 40 can be viewed in the ultrasound system 500 in real time as it is penetrated into the uterine fibroid 18 inside the uterus 17. The therapeutic needle 14 may be penetrated in several configurations (e.g., lateral, side, axially extending) depending on the ultrasound viewing angle. Advantageously, tilting of the ultrasound array 80 and angling of the distal tip 26 allows a treating physician to image most or all of the cornua and fundus of the uterus 17 with a single device 10.

Now referring back to the previous Figures, Table I below illustrates possible viewing angles κ that may be achieved by the cumulative effects of the shaft bending angle β (e.g., either through active deflection of the distal tip or a preshaped or pre-bent distal tip) and the ultrasound tilting angle α. The matching needle angles θ based on the possible viewing angles κ are further illustrated. In example 1, the shaft 24 is in a straight configuration so that the viewing angle κ is provided solely by the tilting angle α of the ultrasound array 80. In example 4, the needle 14 will have a straight configuration. In example 5, a non-tilted and non-bent ultrasound array 80 version is covered. It will be appreciated that the viewing angle κ will be more than the bend angle β of the shaft 24 due to the additive effect of the tilting angle α of the ultrasound array 80. This allows the bend on the distal tip 28 of the shaft 24 to be shallower without compromising the cumulative viewing angle κ, which is of particular benefit for patient insertion considerations. In the case of a deflectable distal tip 28 in which insertion may be implemented in a straight configuration, the tiled ultrasound angle α still aids in reducing the needle angle θ.

TABLE 1

| Example | Viewing Angle (κ) | Tilt Angle (α) | Bend Angle (β) | Needle Angle (θ) |
|---|---|---|---|---|
| 1 | 7°-10° | 7°-10° | 0° | 80° |
| 2 | 20° | 7°-10° | 10°-13° | 70° |
| 3 | 45° | 7°-10° | 35°-38° | 45° |
| 4 | 90° | 7°-10° | 80°-83° | 0° |
| 5 | 0° | 0° | 0° | 90° |

Figure 10A:
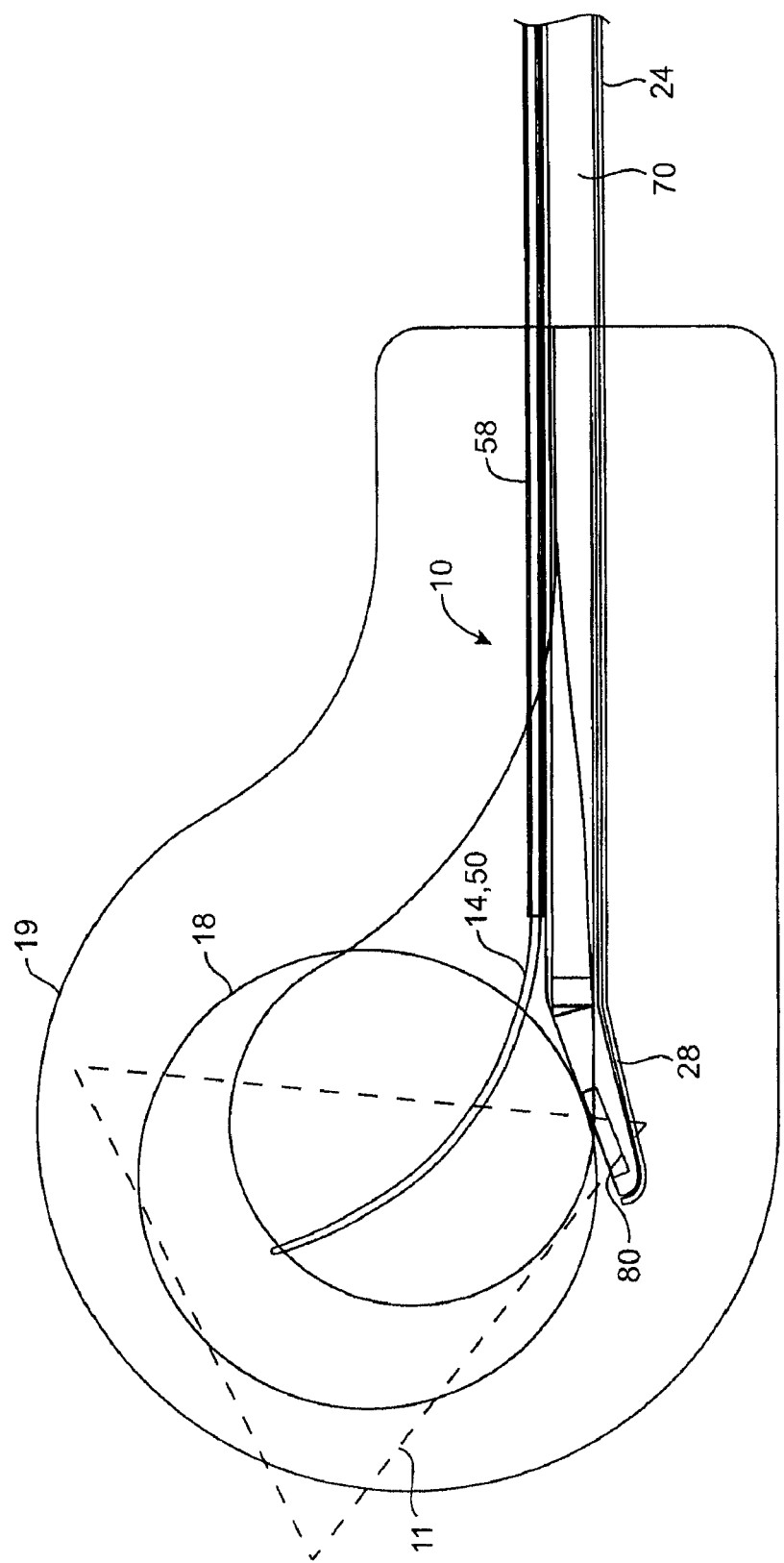
FIGS. 10A through 10C illustrate use of the system of FIG. 1A within a uterus for the treatment of fibroids in accordance with the principles of the present invention.
Figure 10B:
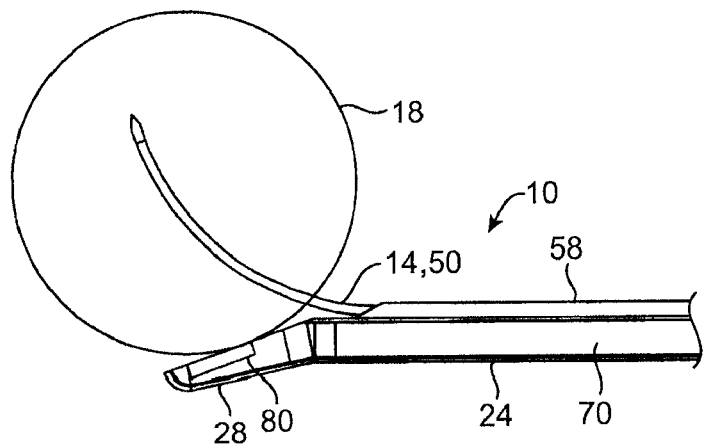
Figure 10C:
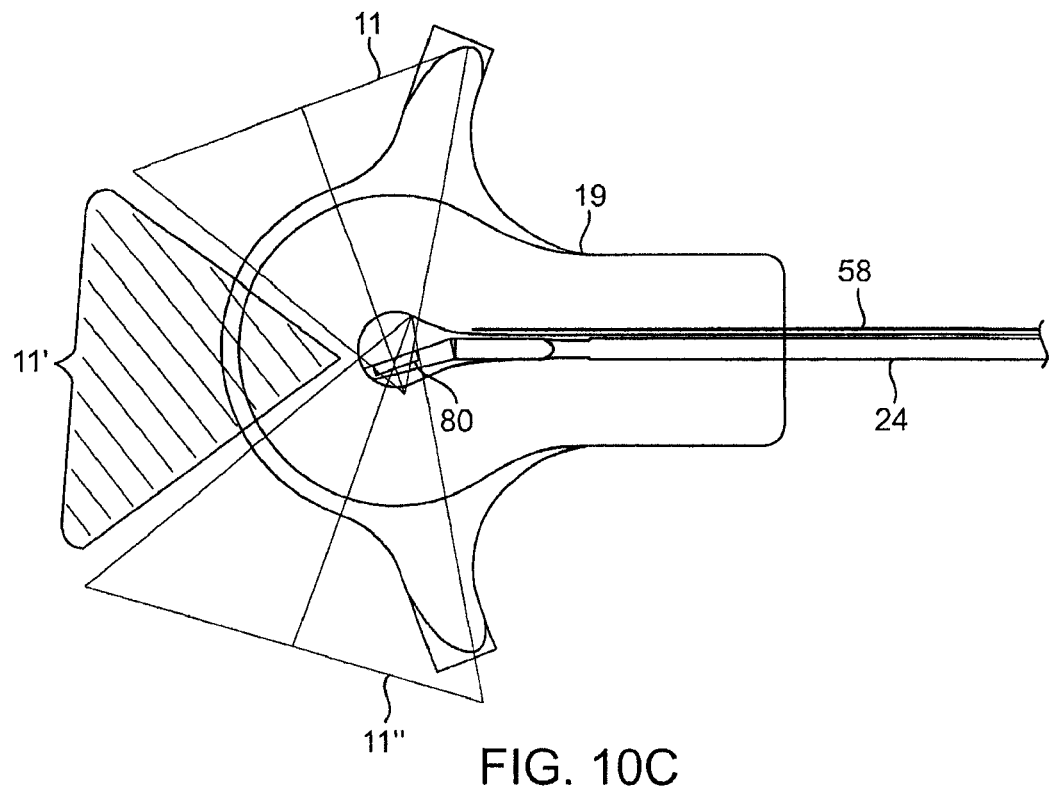

Referring now to FIGS. 10A and 10C, a method, embodying features of the present invention, for using the system 10 of FIG. 1A to treat fibroids or tumors 18 within the uterus 19 is illustrated. Typically, the rigid shaft 24 is inserted in a straight configuration within the uterus 19. The distal tip 28 of the rigid shaft 24 may then be selectively deflected by a pull wire. The ultrasound imaging insert 70 may then be loaded within the axial passage 32 of the shaft 24 prior to, concurrent with, or subsequent to shaft 24 insertion, wherein a distal portion of the insert 70 conforms to the deflected shaft distal end 28. Loading may further involve axially or rotationally aligning the ultrasound imaging insert 70 within the rigid shaft 24. A needle angle θ is then selected by the physician from a plurality of needles 14 having different curvatures based on the shaft bending angle β and the ultrasound tilting angle α. The selected curved needle 14 is then loaded within the passage 59 of the needle guide 58.

In exemplary embodiments, the therapeutic needle 14 advancement from the guide 58 via needle advancement button on the shaft handle 40 can be viewed in real time as it is penetrated into the uterine fibroid 18 inside the uterus 19 as illustrated by the viewing plane 11 in FIGS. 10A and 10B. The therapeutic needle 14 may be penetrated in several configurations (e.g., lateral, side, axially extending) depending on the ultrasound viewing angle κ. Advantageously, tilting of the ultrasound array 80 and angling of the distal tip 28 allows a treating physician to image most or all of the cornua and fundus of the uterus 19 with a single device 10. As shown in FIG. 10C, the device 10 may be configured so as to provide the desired viewing angle κ (e.g., distally forward direction, side-viewing or lateral direction). It will further be appreciated that manipulation of the device 10, as for example, torquing and/or rotating the rigid device 16 in addition to tip deflection and ultrasound tilt a will allow a physician to obtain the desired viewing planes 11, 11', 11". For example, viewing plane 11" may be achieved if the device 10 was rotated 180° about its axis. Further, viewing plane 11' may be achieved by torquing the device 10.

Figure 11A:
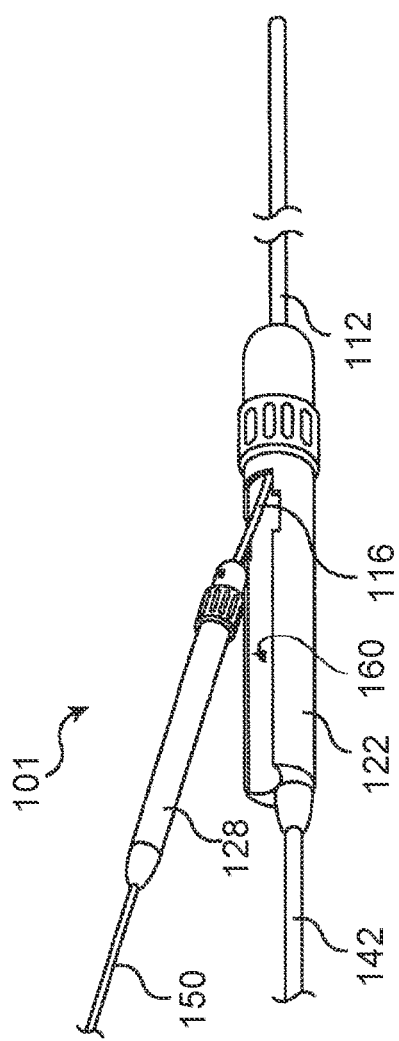
FIGS. 11A through 11C illustrate insertion of an imaging core into a sheath where both the imaging core and an interventional core extend axially from a distal end of the sheath, wherein the interventional core comprises a straight needle.
Figure 11B:
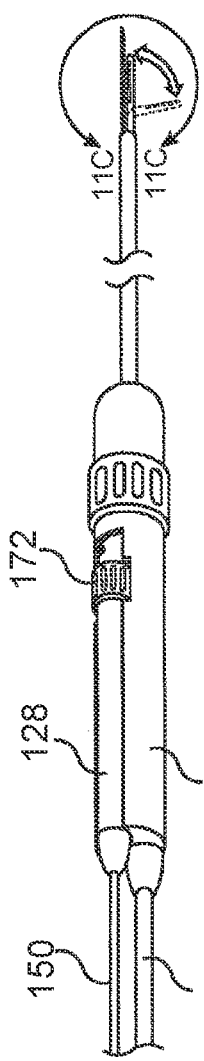
Figure 11C:
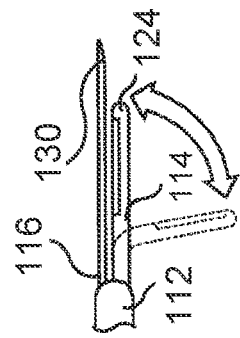

Referring now to FIGS. 11A through 11C, an embodiment 101 of the needle deployment and imaging system of the present invention includes sheath 112, imaging core 114, and interventional core 116 which are in many ways the same as described previously except for the distal end deployment configurations. As shown in FIG. 11A, imaging core 114 is loaded into the sheath 112 where that the sheath 112 does not necessarily include an acoustically or optically transparent window at its distal end. Instead as best shown in FIG. 11B, both the distal end 130 of the interventional core 116 and the distal end 124 of the imaging core 114 are extendable through ports in the distal end of the sheath 112. Moreover, the distal end 124 of the imaging core 114 is deflectable using the control knob 172 of the handle structure 128, as shown in broken line. The distal end of the sheath 112 will often be steerable, and the embodiment of the needle deployment and imaging system 101 will allow access to a variety of tissue surfaces within the uterine or other body cavities by steering of the sheath, deflection of the imaging core, and rotation of the imaging core relative to the sheath. The handle structure 128 of the imaging core 114 is joined to a handle structure 122 of the sheath 112 to properly position the needle 130 relative to the sheath 112 prior to use. For example, the handle structure 128 may be placed in a cradle 160 of the handle structure 122 so that an assembly handle is formed as shown in FIG. 11B.

Although certain exemplary embodiments and methods have been described in some detail, for clarity of understanding and by way of example, it will be apparent from the foregoing disclosure to those skilled in the art, that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A method of treating a uterine fibroid, said method comprising:
    delivering an ultrasonic imaging device and a radiofrequency ablation device coupled together into a uterine cavity, wherein the ultrasonic imaging device comprises an ultrasonic transducer and the radiofrequency ablation device comprises one or more needle electrodes;
    deflecting a distal end of the ultrasonic imaging device to orient the ultrasonic transducer;
    deploying the one or more needle electrodes into a uterine fibroid while the ultrasonic imaging device provides a real time image of the uterine fibroid; and
    delivering radiofrequency energy to the one or more needle electrodes.

2. The method of claim 1, wherein the radiofrequency ablation device is contained within a sheath when delivered.

3. The method of claim 2, wherein the one or more needle electrodes are reciprocatably advanced relative to the sheath when the one or more needle electrodes are deployed into the uterine fibroid.

4. The method of claim 3, wherein the one or more needle electrodes are advanced laterally relative to the sheath when deployed into the uterine fibroid.

5. The method of claim 3, wherein the one or more needle electrodes are advanced axially relative to the sheath when deployed into the uterine fibroid.

6. The method of claim 1, wherein deploying the one or more needle electrodes into the uterine fibroid comprises advancing a plurality of needle electrodes into the uterine fibroid.

7. The method of claim 1, wherein the one or more needle electrodes are advanced laterally relative to an access direction of the radiofrequency ablation device when the one or more needle electrodes are deployed into the uterine fibroid.

8. The method of claim 7, wherein a plurality of needle electrodes are advanced laterally relative to an access direction of the radiofrequency ablation device when the one or more needle electrodes are deployed into the uterine fibroid.

9. The method of claim 1, wherein the one or more needle electrodes are advanced forwardly and laterally relative to an access direction of the radiofrequency ablation device when the one or more needle electrodes are deployed into the uterine fibroid.

10. The method of claim 9, wherein a plurality of needle electrodes are advanced forwardly and laterally relative to an access direction of the radiofrequency ablation device when the one or more needle electrodes are deployed into the uterine fibroid.

11. The method of claim 1, wherein the ultrasonic imaging device is removably fixed relative to the radiofrequency ablation device when the ultrasonic imaging device and the radiofrequency ablation device are delivered into the uterine cavity.

12. The method of claim 11, further comprising, prior to delivering the ultrasonic imaging device and the radiofrequency ablation device into the uterine cavity, coupling the ultrasonic imaging device and the radiofrequency ablation device together.

13. The method of claim 12, wherein coupling the ultrasonic imaging device and the radiofrequency ablation device together comprises removably coupling a handle of the ultrasonic imaging device to a handle of the radiofrequency ablation device.

14. The method of claim 1, further comprising, after delivering the radiofrequency energy to the one or more needle electrodes, uncoupling the ultrasonic imaging device from the radiofrequency ablation device.

15. The method of claim 14, further comprising, after uncoupling the ultrasonic imaging device from the radiofrequency ablation device, disposing of the radiofrequency ablation device.

16. The method of claim 15, further comprising, after uncoupling the ultrasonic imaging device from the radiofrequency ablation device, sterilizing the ultrasonic imaging device for reuse.

17. The method of claim 14, wherein, after uncoupling the ultrasonic imaging device from the radiofrequency ablation device, the radiofrequency ablation device is disposable.

18. The method of claim 14, wherein, after uncoupling the ultrasonic imaging device from the radiofrequency ablation device, the ultrasonic imaging device is sterilizable for reuse.

19. A method of treating a uterine fibroid, comprising:
    delivering an ultrasonic imaging device and a radiofrequency ablation device coupled together into a uterine cavity, wherein the ultrasonic imaging device comprises an ultrasonic transducer and the radiofrequency ablation device comprises one or more needle electrodes;
    deflecting a distal end of the ultrasonic imaging device to orient the ultrasonic transducer; and
    deploying the one or more needle electrodes into a uterine fibroid while the ultrasonic imaging device provides a real time image of the uterine fibroid.

20. A method of treating a uterine fibroid, comprising:
    delivering an ultrasonic imaging device and an ablation device coupled together into a uterine cavity, wherein the ultrasonic imaging device comprises an ultrasonic transducer and the ablation device comprises one or more needle electrodes;
    deflecting a distal end of the ultrasonic imaging device to orient the ultrasonic transducer;
    deploying the one or more needle electrodes into a uterine fibroid while the ultrasonic imaging device provides a real time image of the uterine fibroid; and
    delivering energy to the one or more needle electrodes.

* * * * *

UNITED STATES PATENT AND TRADEMARK OFFICE
CERTIFICATE OF CORRECTION

| | |
|---|---|
| PATENT NO. | : 11,259,825 B2 |
| APPLICATION NO. | : 15/628166 |
| DATED | : March 1, 2022 |
| INVENTOR(S) | : Robert K. Deckman et al. |

It is certified that error appears in the above-identified patent and that said Letters Patent is hereby corrected as shown below:

On the Title Page

Item (63) Related U.S. Application Data, page 2, Column 1, Line 8:
Delete "11/620,591" and insert -- 11/620,594 --

Signed and Sealed this
Nineteenth Day of March, 2024

Katherine Kelly Vidal
*Director of the United States Patent and Trademark Office*